(12) United States Patent
Onuki et al.

(10) Patent No.: US 7,776,066 B2
(45) Date of Patent: *Aug. 17, 2010

(54) ENDOSCOPIC SUTURE APPARATUS

(75) Inventors: Yoshio Onuki, Hino (JP); Hitoshi Mizuno, Koganei (JP); Hideki Shimonaka, Hachioji (JP)

(73) Assignee: Olympus Corporation, Tokyo (JP)

( * ) Notice: Subject to any disclaimer, the term of this patent is extended or adjusted under 35 U.S.C. 154(b) by 457 days.

This patent is subject to a terminal disclaimer.

(21) Appl. No.: 11/411,638

(22) Filed: Apr. 26, 2006

(65) Prior Publication Data

US 2006/0190016 A1 Aug. 24, 2006

Related U.S. Application Data

(63) Continuation of application No. 10/616,517, filed on Jul. 10, 2003, now Pat. No. 7,063,715.

(60) Provisional application No. 60/395,077, filed on Jul. 11, 2002.

(51) Int. Cl.
*A61B 17/08* (2006.01)
*A61D 1/00* (2006.01)

(52) U.S. Cl. ............... 606/220; 606/139; 606/142; 606/144; 606/219

(58) Field of Classification Search ......... 606/139–148, 606/217, 220, 225, 232
See application file for complete search history.

(56) References Cited

U.S. PATENT DOCUMENTS

| 4,235,238 | A | 11/1980 | Ogiu et al. | |
|---|---|---|---|---|
| 4,841,888 | A | * | 6/1989 | Mills et al. ................. 112/169 |
| 5,792,153 | A | | 8/1998 | Swain et al. |
| 6,719,763 | B2 | | 4/2004 | Chung et al. |
| 6,755,843 | B2 | | 6/2004 | Chung et al. |
| 7,063,715 | B2 | * | 6/2006 | Onuki et al. ................. 606/220 |

FOREIGN PATENT DOCUMENTS

| JP | 6-44913 | 6/1994 |
|---|---|---|
| JP | 11-313826 | 11/1999 |
| JP | 2002-523171 | 7/2002 |

* cited by examiner

*Primary Examiner*—Todd E Manahan
*Assistant Examiner*—Michael G Mendoza
(74) *Attorney, Agent, or Firm*—Scully, Scott, Murphy & Presser, P.C.

(57) ABSTRACT

A holding member has an opening portion which opens to an distal end. The opening portion, the distal end of an endoscope and a holding member define a treatment space. A clamping member can project and retreat from and into the opening portion through the treatment space. The puncture member can move in the treatment space, in a direction that intersects with the longitudinal direction of the endoscope.

11 Claims, 18 Drawing Sheets

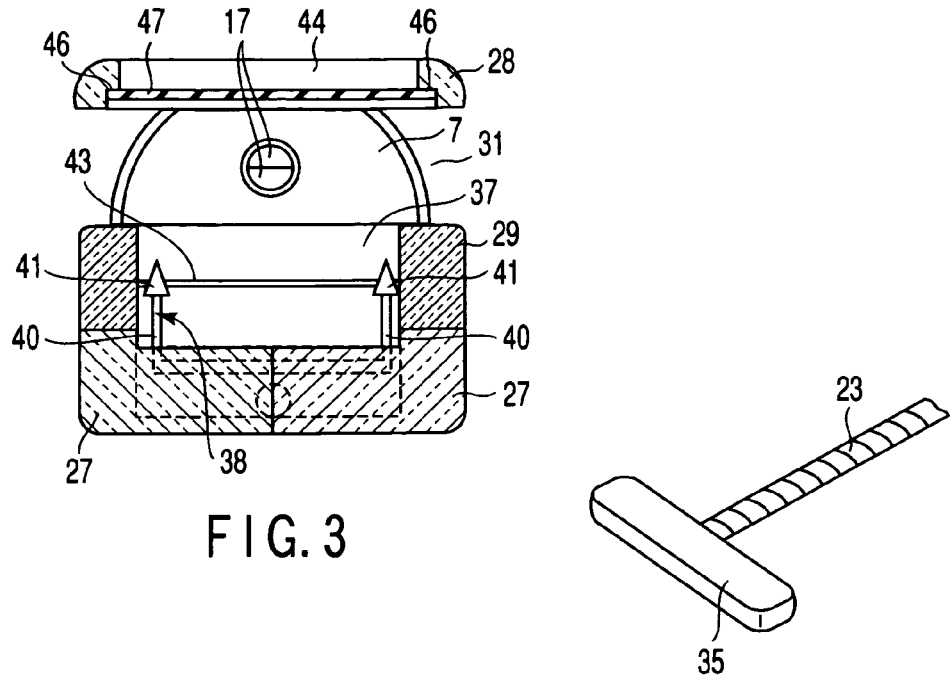
FIG. 3
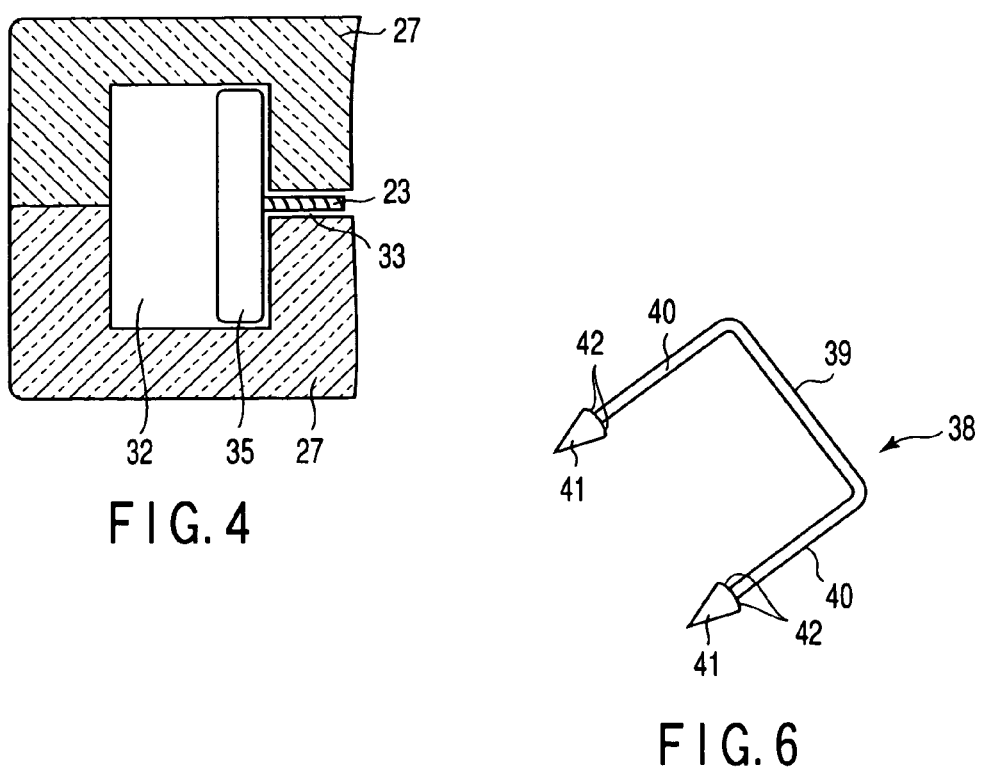
FIG. 5
FIG. 4
FIG. 6

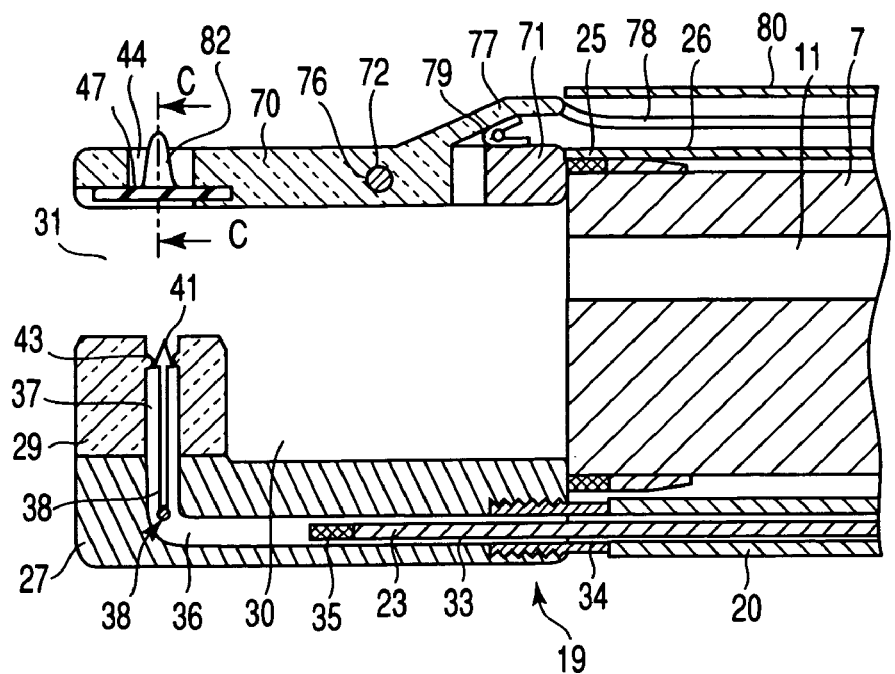
F I G. 14
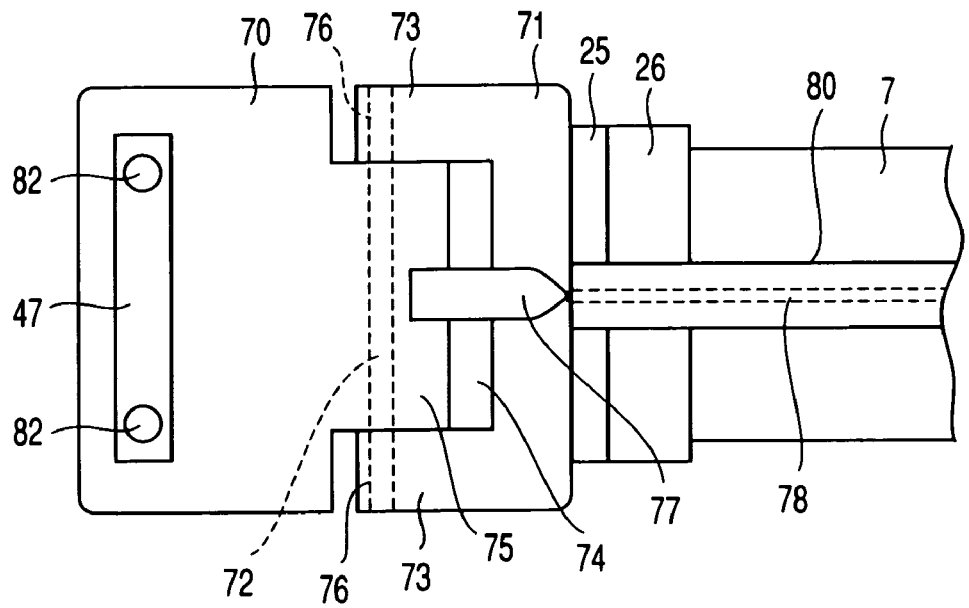
F I G. 15

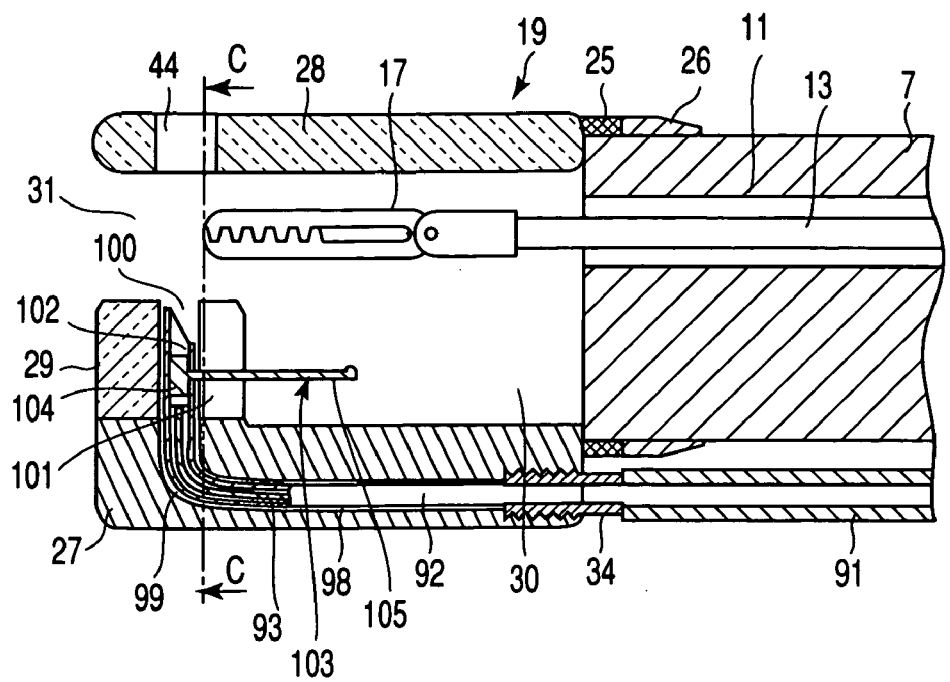
F I G. 20
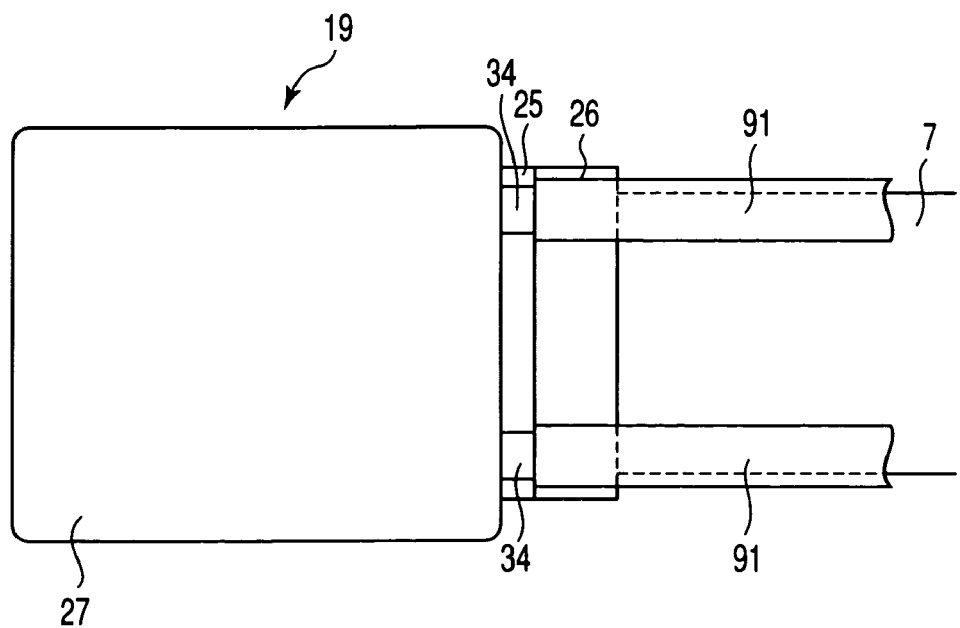
F I G. 21

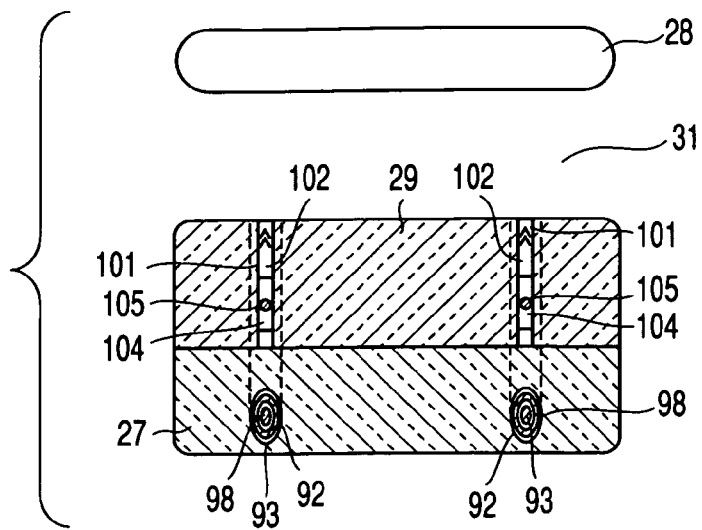
FIG. 22
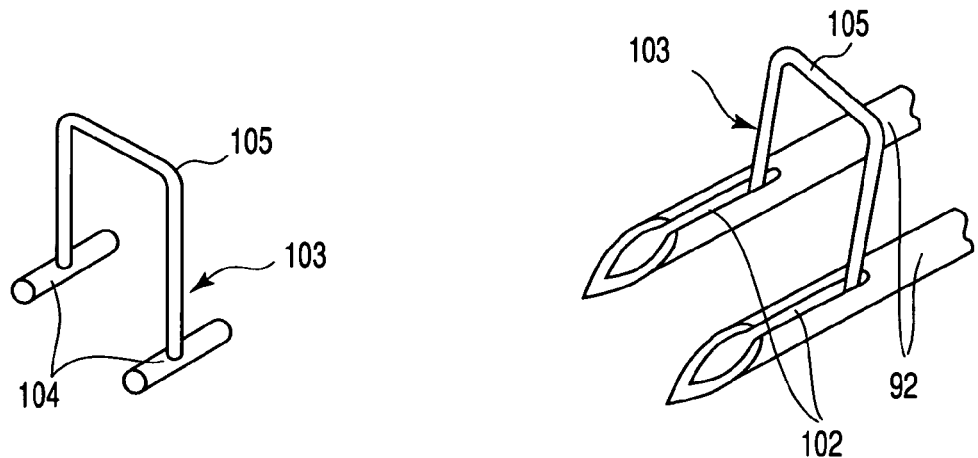
FIG. 23A
FIG. 23B
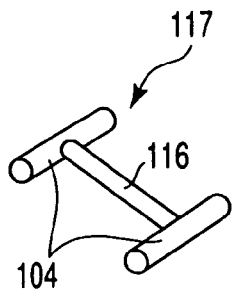
FIG. 23C

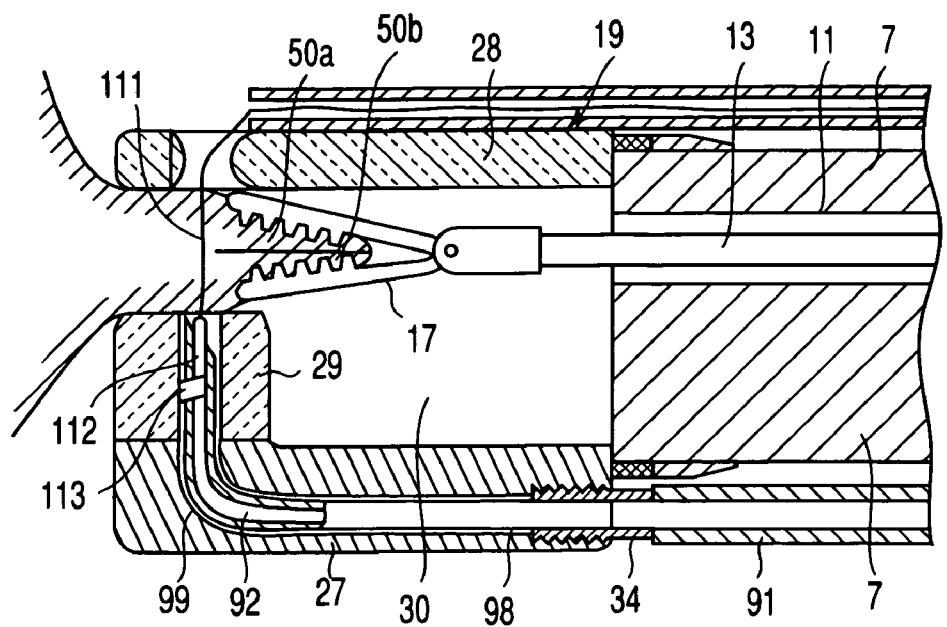
FIG. 33
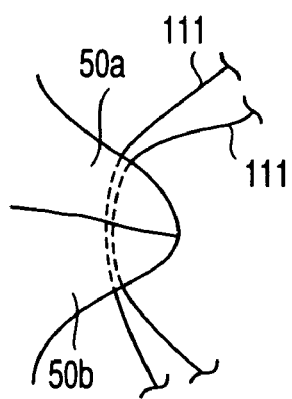   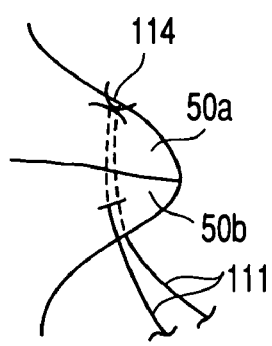   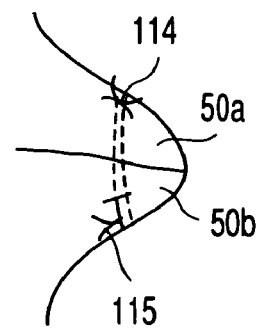
FIG. 34A    FIG. 34B    FIG. 34C

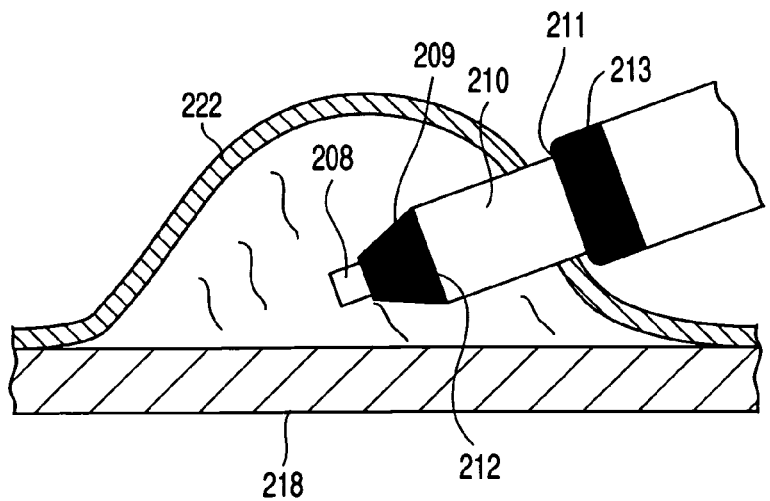
F I G. 40
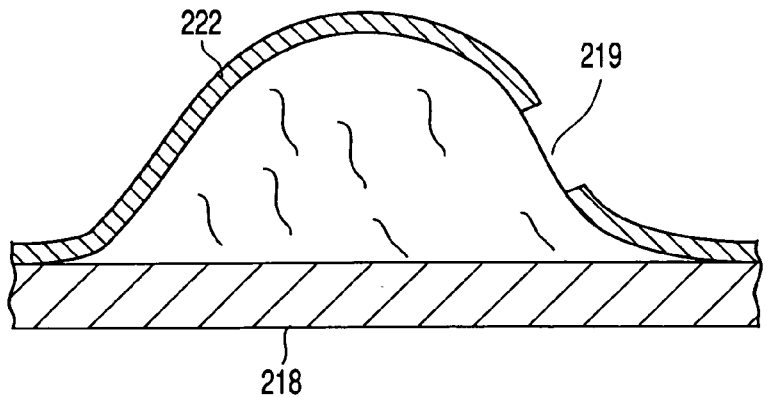
F I G. 41
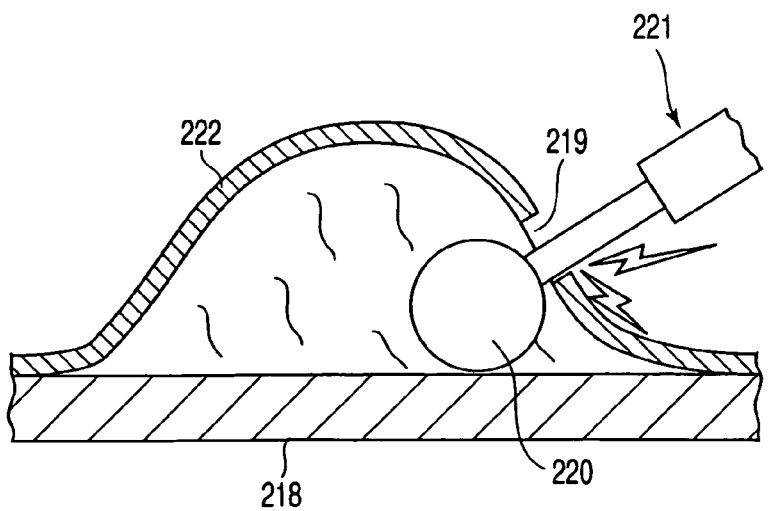
F I G. 42

ENDOSCOPIC SUTURE APPARATUS

CROSS-REFERENCE TO RELATED APPLICATIONS

This application is a Continuation Application of U.S. Ser. No. 10/616,517 filed Jul. 10, 2003, now U.S. Pat. No. 7,063,715 which claims the benefit of U.S. Provisional Application No. 60,395,077, filed Jul. 11, 2002, each of which is incorporated herein by their reference.

BACKGROUND OF THE INVENTION

1. Field of the Invention

The present invention relates to an endoscopic suture apparatus that can be endoscopically inserted into a living body cavity and can suture or ligate organic tissues. More particularly, the invention relates to an endoscopic suture apparatus for performing suture to treat a damaged part of the tissue of the digestive canal or to reliably arrest hemorrhage in a bleeding region and to form an artificial valve in the treatment of a gastro-esophageal reflux disease.

2. Description of the Related Art

In general, tissues in the body of a patient are sutured in a surgical operation nowadays. Naturally, the patient's body cavity must be incised in the case of the surgical operation. The patient inevitably suffers a heavy invasion. Further, the patient must bear considerable costs including expenses of postoperative hospitalization that is required.

In view of this, it is desired that a medical treatment method be established, which uses a low-invasion oral endoscope and which obviates the necessity of incision of the patient's body.

The gastro-esophageal reflux disease (GERD) is one of diseases that affect more and more people these days. The principal symptoms of this disease include heartburn and mucosal break in the gullet. The disease is characterized in that it causes heavy pain to patients despite its benignancy. Hence, many patients require treatment. The main cause is a decrease in the function of the lower esophageal sphincter (LES) in the lower part of the gullet, which makes gastric acid flow upstream into the gullet.

A gastric-acid secretion inhibitor such as a proton-pump inhibitor is administered for treatment for the GERD. If the GERD is mild, its symptoms can be mitigated. A radical cure can be expected. However, a case wherein the function of the LES is lowered considerably and a serious case, such as a hiatal hernia, which involves an anatomical problem, can enjoy only a low effect of medication. These cases requires continuous administration, inevitably entailing high cost. Therefore, a surgical operation is applied to a serious GERD case. The Nissen fundoplication and Toupet methods are widely used as effective techniques.

In either method, the function of the LES is improved by wrapping the LES portion in the wall of the stomach, achieving a high curative effect. Recently, the laparoscopic technique has been established for treatment of lower invasion. However, there are numerous patients, and this disease is a benign disease, unlike cancer. There is a demand for the establishment of a method of treatment using a lower-invasion oral endoscope. To meet the demand, a method, or a technique, has been devised. In this method, a backward flow of gastric acid is prevented by using an artificial valve that is formed by ligating and bulging an organic tissue.

U.S. Pat. No. 5,792,153 (PCT National Publication No. 10-500318), Jpn. Pat. Appln. KOKOKU Publication No. 6-44,913, and Jpn. Pat. Appln. KOKAI Publication No. 11-313,826, for example, disclose endoscopic suture apparatuses.

The suture apparatus disclosed in U.S. Pat. No. 5,792,153 (PCT National Publication No. 10-500318) and Jpn. Pat. Appln. KOKOKU Publication No. 6-44,913 is mounted on the far-side end of the endoscope. This suture apparatus has a cavity having an opening in the flank. The cavity connects a biopsy channel and a suction channel. The cavity is subjected to vacuum suction through the suction channel. A part of an organic tissue is thereby drawn, in the shape of a U, into the cavity. A needle and a thread carrier in the biopsy channel are stabbed into the U-shaped part to suture the channel.

As described in Jpn. Pat. Appln. KOKAI Publication No. 11-313,826, a cap is provided on the tip of the endoscope, and a cavity having an opening is provided in the flank of the cap. In the tip, a suture tool is held by a holding forceps that is provided on the distal end portion of a sheath.

The organic tissue is sucked into the cavity through the opening made in the flank of the cap. The suture tool is stabbed into the organism tissue by using the holding forceps.

Any apparatus described in U.S. Pat. No. 5,792,153 (PCT National Publication No. 10-500318), Jpn. Pat. Appln. KOKOKU Publication No. 6-44,913, and Jpn. Pat. Appln. KOKAI Publication No. 11-313,826 is designed so that the organism tissue is sucked into the cavity having the opening in the flank of the tip portion of the endoscope.

Therefore, the cavity must be positioned, with the opening opposing a target region of the organism tissue, and then be depressurized. Thus, the opening of the cavity can hardly be moved to the target region. Consequently, the organism tissue cannot be fully drawn into the cavity when the cavity is depressurized only.

Further, a part of the stomach must be sucked in suturing the organism tissue to form an artificial valve for use in treatment of, for example, a gastro-esophageal reflux disease. However, the stomach wall is thicker than the tissues of the gullet and the like and is composed of a lumen-side mucous membrane, intermediate proper muscularis, and coat-side serous membrane. High fluidity is present, in particular between the mucous membrane and the proper muscular. To form a boss of a size suitable as a valve, it is essential to shorten and swell the tissue after capturing the proper muscularis. The conventional apparatuses can indeed capture the mucous membrane. However, it cannot easily capture the proper muscularis that underlies the mucous membrane. It is quite probable that the valve thus formed cannot be large and thick enough to prevent a backward flow reliably. To suture a damaged part securely, for example, it is necessary to suture the tissue including the proper muscularis or serous membrane. With the conventional apparatuses, however, it is difficult to capture the proper muscularis or serous membrane.

The object of the present invention is to provide an endoscopic suture apparatus capable of easily approaching a target region of an organic tissue and capturing the organism tissue in a holding portion to suture it.

According to an aspect of this invention, there is provided a endoscopic suture apparatus which comprises: an endoscope; a puncture member which has at least one sharp tip; a holding member which holds the puncture member and which is removably attached to an distal end of the endoscope; a clamping member which is configured to move back and forth with respect to the endoscope and to clamp living tissues; and a drive member which is configured to move the puncture member. The holding member has an opening portion which opens to an distal end. The opening portion, the distal end of the endoscope and the holding member define a treatment space. The clamping member is configured to project and retreat from and into the opening portion through the treatment space. The puncture member is configured to move in the treatment space, in a direction that intersects with a longitudinal direction of the endoscope.

BRIEF DESCRIPTION OF THE SEVERAL VIEWS OF THE DRAWING

FIG. 3 is a sectional view of the same embodiment taken along line A-A of FIG. 2;

FIG. 4 is a sectional view of the same embodiment taken along line B-B of FIG. 2;

FIG. 5 is a perspective view of a pusher according to the same embodiment;

FIG. 6 is a perspective view of a staple according to the same embodiment;

FIG. 14 is a longitudinal sectional side view of the distal end portion of the suture apparatus according to the same embodiment;

FIG. 15 is a plan view of the distal end portion of the suture apparatus according to the same embodiment;

FIG. 20 is a longitudinal sectional side view of the distal end portion of the suture apparatus according to the same embodiment;

FIG. 21 is a plan view of the distal end portion of the suture apparatus according to the same embodiment;

FIG. 22 is a sectional view of the same embodiment taken along line C-C of FIG. 20;

FIG. 23A is a perspective view of a staple according to the same embodiment;

FIG. 23B is a perspective view of a hollow needle;

FIG. 23C is a perspective view of a staple;

FIG. 33 is a longitudinal sectional side view of the distal end portion of the suture apparatus, showing the function of the same embodiment;

FIGS. 34A, 34B and 34C are side views showing the function of the same embodiment and illustrating steps of procedure for suture;

FIG. 40 is a view illustrating the operation for endoscopic mucosal resection;

FIG. 41 is a view illustrating the operation for endoscopic mucosal resection; and FIG. 42 is a view illustrating the operation for endoscopic mucosal resection.

DETAILED DESCRIPTION OF THE INVENTION

Figure 1:
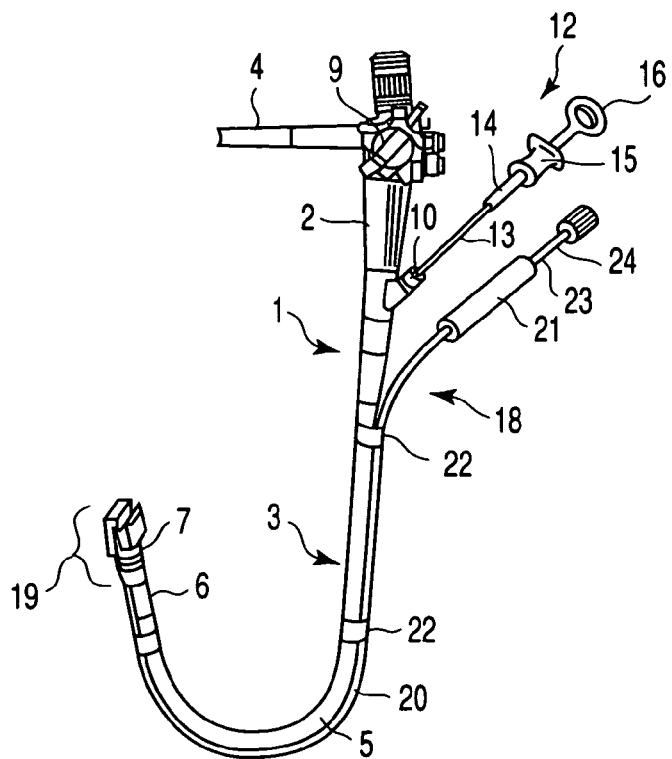
FIG. 1 a perspective view of an endoscopic suture apparatus according to a first embodiment of the present invention.

Embodiments of the present invention will now be described with reference to the drawings.

FIGS. 1 to 10 show a first embodiment of an endoscopic suture apparatus. An endoscope 1 shown in FIG. 1 comprises a control section 2, a flexible insertion section 3, and a universal cord 4. The insertion section 3 is composed of a flexible tube portion 5, a bending tube portion 6, and a tip portion 7. The control section 2 has a bending control portion 9 and a forceps tap 10.

Figure 2:
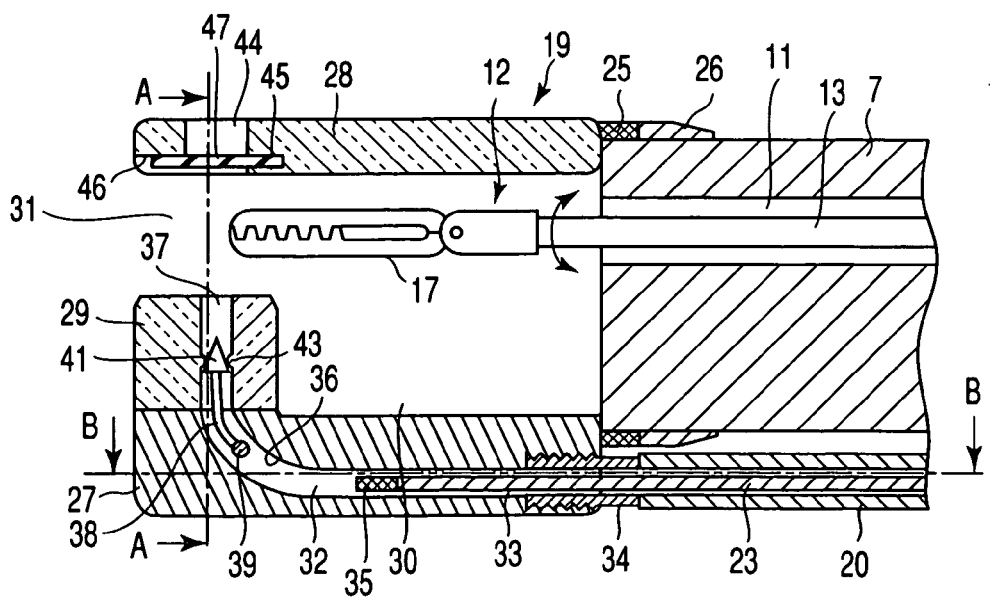
FIG. 2 is a longitudinal sectional side view of a distal end portion of the suture apparatus according to the same embodiment.

As shown in FIG. 2, the forceps tap 10 communicates with a forceps channel 11 that in connected to the tip portion 7 by the insertion section 3. The sheath 13 of a grasping forceps 12 passes through the forceps tap 10. The grasping forceps 12 is used as a clamping member. The sheath 13 is formed of metallic multiple coils or a plastic tube studded with blades, for example. A control section body 14 is provided on the near-side end of the sheath 13, and is fitted with a slider 15 and a finger ring 16.

A grasping portion 17 in the form of a nipper-type forceps is provided on the far-side end of the grasping forceps 12. The grasping portion 17 can be opened or closed as the slider 15 is moved. Further, the grasping portion 17 can be rotated to change its course as the control section body 14 is turned.

The insertion section 3 of the endoscope 1 incorporates a puncture device 18. The puncture device comprises a cap 19, a sheath 20, and a puncture control portion 21. The cap 19 serves as a holding member that is removably attached to the tip portion 7 of the endoscope 1. The sheath 20 is formed of a flexible material such that it can follow the bending motion of the insertion section 3. The material may, for example, be a plastic tube of fluoroplastic, polyethylene, polyamide, polyimide, polyurethane, any of various thermoplastic elastomers, or a metallic coil. Alternatively, the sheath 20 may be a plastic tube that is reinforced with a metallic mesh lest it easily kink.

The sheath 20 is fixed to the insertion section 3 of the endoscope 1 with a medical tape 22. The puncture control portion 21 is held near the control section body 14 of the grasping forceps 12. A sheath joint 34 is coupled to the distal end of the sheath 20.

A pusher member 23 for use as moving member (member for driving the puncture-member) is movably fitted in the sheath 20. The pusher member 23 is formed of a metallic stranded wire or the like. Its near-side end is coupled to a control slider 24 of the puncture control portion 21.

The cap 19 is made of relatively rigid material. Preferably, it should be made of highly transparent material, such as polycarbonate or norbornane resin, lest it should obstruct the view of the endoscope. The cap 19 is shaped like a rectangular box. A cylindrical attachment 26 is secured on its proximal end portion by means of a connecting member 25. The cap 19 can be removably attached to the endoscope 1 by fitting the attachment 26 on the tip portion 7.

As shown in FIGS. 2 and 3, the cap 19 has flat lower and upper bases 27 and 28. The bases 27 and 28 are separated left and right and opposed to each other. A tip base 29 protrudes from the distal end portion of the lower base 27 toward the upper base 28. The cap 19 therefore has a treatment space 30 that is defined by the lower and upper bases 27 and 28 and the tip base 29. Provided between the lower and upper bases 27 and 28 is an opening portion 31 that opens to the distal end and connects with the treatment space 30. The opening portion 31 opposes the forceps channel 11 of the tip portion 7. The grasping portion 17 can therefore project and retract through it.

As shown in FIG. 4, the lower base 27 of the cap 19 has a guide bore 32. The bore 32 is broad in the horizontal direction and narrow in the vertical direction. A through hole 33 that faces the sheath 20 of the puncture device 18 is made in the middle of the proximal end portion of the guide bore 32 with respect to the width direction. The sheath joint 34 is set in screw engagement with the through hole 33 and connected to the sheath 20. Thus, the pusher member 23 that is passed through the sheath 20 extends through the sheath joint 34 to the guide bore 32.

As shown in FIG. 5, a pusher 35 is coupled to the far-side end of the pusher member 23. It can move back and forth in the guide bore 32. The pusher 35 is shaped like a square bar, is fixed to the pusher member 23 at right angles thereto and extends in the width direction of the guide bore 32.

The guide bore 32 has a bent guide bore 36. The bent guide bore 36 is upwardly bent in a circular arc on its distal end. The bent guide bore 36 communicates with a flat vertical guide bore 37 made in the tip base 29.

The bent guide bore 36 contains a staple 38 for use as a puncture member. As FIG. 6 shows, the staple 38 is a substantially U-shaped member. It is formed of metal having elastic restoring force, such as Nitinol, stainless steel or the like The staple 38 has a pair of parallel prongs 40 that extend at right angles to a base portion 39. A pointed head 41 is attached to the distal ends of each prong 40. The pointed head 41 is shaped like an arrowhead or cone. The proximal end face of the pointed head 41 has engaging surfaces 42.

The slopes of the pointed heads 41 of the staple 38 provided in the bent guide bore 36 touch a ridge portion 43 formed on the inner peripheral surface of the vertical guide bore 37. The staple 38 is therefore positioned not to jump out.

Further, the upper base 28 that faces the vertical guide bore 37 has a side aperture 44. A groove portion 45 is provided on the proximal end side of the inner peripheral surface of the side aperture 44. Receiving portions 46 defined by steps are provided on the both sides and the distal end of the side aperture 44, respectively. Further, a receiving sheet 47 closes the side aperture 44. One side of the outer peripheral edge of the receiving sheet 47 is removably inserted into the groove portion 45. The remaining three sides are supported on the receiving portions 46. The receiving sheet 47 is formed of a flexible sheet of resin exhibiting good bio-compatibility, such as nylon, fluoroplastic or silicone. The receiving sheet 47 can be punctured with the staple 38.

How the first embodiment operates will be described.

As FIG. 2 shows, the sheath 20 is fixed to the insertion section 3 of the endoscope 1 by using the medical tape 22. The attachment 26 of the cap 19 is fastened to the tip portion 7. The opening of the forceps channel 11 of the tip portion 7 is set, opposing the opening portion 31 of the cap 19. Then, the staple 38 is put into the bending guide bore 36 of the cap 19. The sheath 20 of the puncture device 18 and the through hole 33 of the cap 19 are connected by means of the sheath joint 34.

Figure 7:
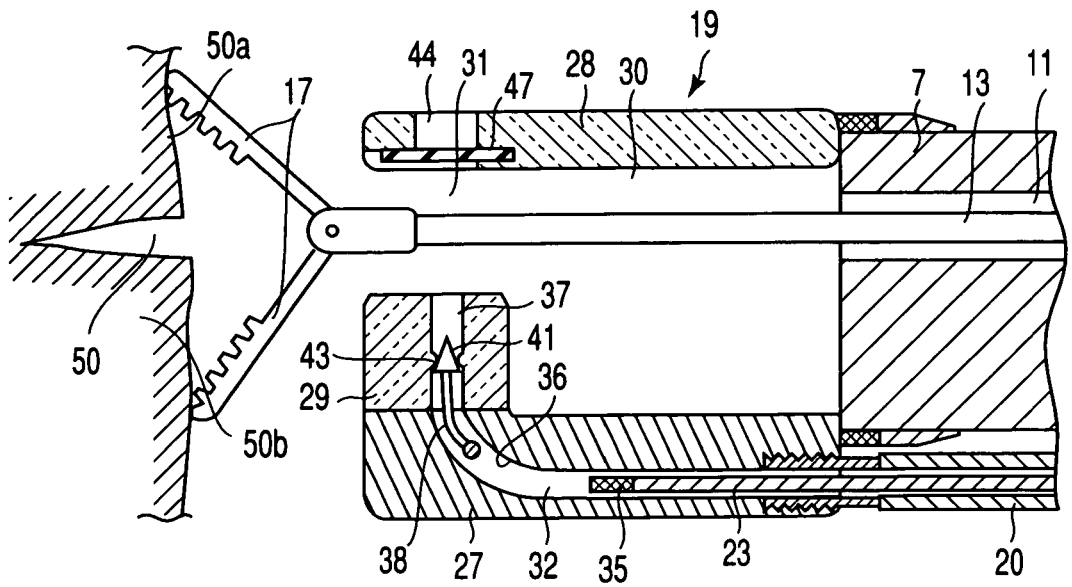
FIG. 7 is a longitudinal sectional side view of the distal end portion of the suture apparatus, showing the function of the same embodiment.

In this state, the insertion section 3 of the endoscope 1 is inserted into the patient's body cavity through the mouth and throat. The bending control portion 9 is operated, guiding the tip portion 7 to a suture region under endoscopic observation. The suture region may be an incised wound 50 of an organic tissue, as illustrated in FIG. 7. To suture tissue portions 50a and 50b on the opposite sides of the incised wound 50, the opening portion 31 of the cap 19 is located close to the incised wound 50.

Then, the control section body 14 of the grasping forceps 12 is operated, moving the sheath 13 forwards. The grasping portion 17 is thus projected forward from the space 30 of the cap 19 through the opening portion 31. The control section body 14 is then be turned. In this case, the sheath 13 can re-direct the grasping portion 17, making the same facing the tissue portions 50a and 50b.

In this state, the surgeon puts the fingers on the finger ring 16 and on the slider 15. He or she pushes the slider 15 forward, opening the grasping portion 17 and pressing the grasping portion 17 against the tissue portions 50a and 50b. If the slider 15 is then moved backward, the grasping portion 17 is closed. When the portion 17 is closed, it holds the tissue portions 50a and 50b.

Figure 8:
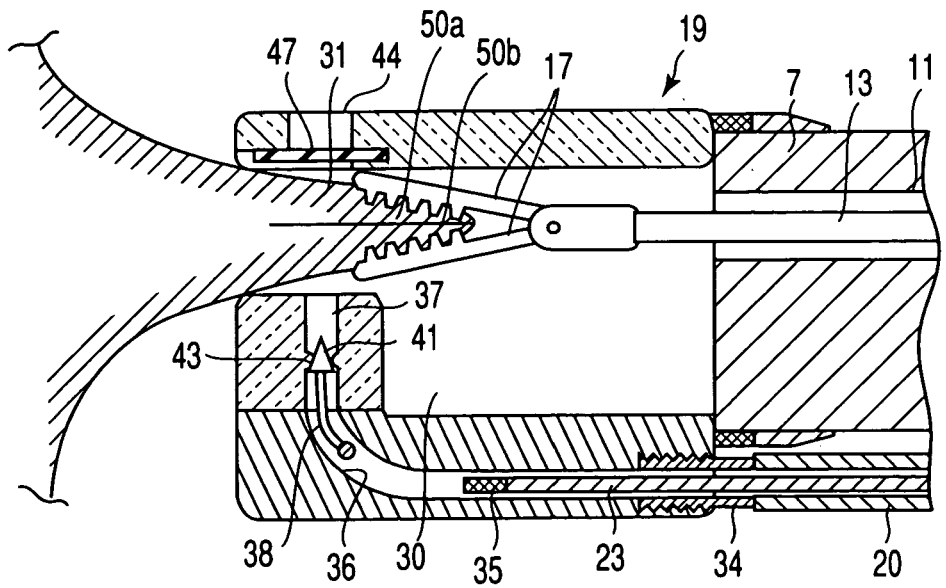
FIG. 8 is a longitudinal sectional side view of the distal end portion of the suture apparatus, showing the function of the same embodiment.

The control section body 14 may be then pulled to the hand side, as shown in FIG. 8. If so, the grasping portion 17 is retreated by the sheath 13. The tissue portions 50a and 50b, both held by the grasping portion 17, can be pulled into the space 30 of the cap 19 through the opening portion 31. If the control slider 24 is advanced, while supporting the puncture control portion 21 of the puncture device 18, the pusher member 23 moves forward in the sheath 20.

As the pusher member 23 moves forward, the pusher 35 moves from the guide bore 32 to the bent guide bore 36. The pusher 35 abuts on the base portion 39 of the staple 38. If the pusher 35 is further moved forward, the pointed heads 41 of the staple 38 get over the ridge portion 43 of the vertical guide bore 37, projecting into the opening portion 31 through the vertical guide bore 37.

Figure 9:
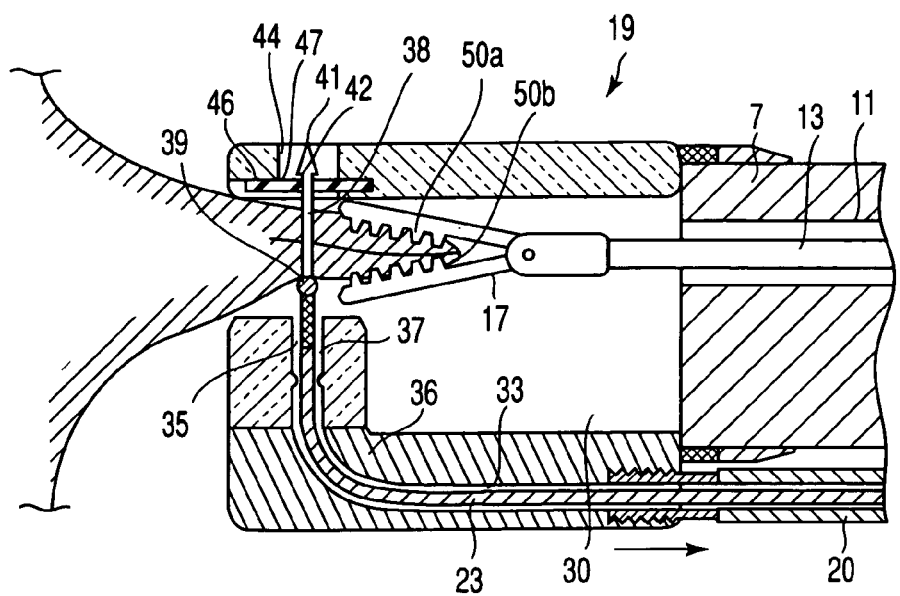
FIG. 9 is a longitudinal sectional side view of the distal end portion of the suture apparatus, showing the function of the same embodiment.

The staple 38 is thus stabbed into the tissue portions 50*a* and 50*b* that are pulled into the space 30 of the cap 19. The pointed heads 41 penetrate the tissue portions 50*a* and 50*b* and then penetrate the receiving sheet 47, as is illustrated in FIG. 9.

As the staple 38 are pushed onto the tissue portions 50*a* and 50*b*, both tissue portions 50*a* and 50*b* are pushed in the same direction the staple 38. Nonetheless, the upper base 28 holds the staple 38, enabling the staple 38 to penetrate the tissue portions 50*a* and 50*b*.

If the slider 15 of the grasping forceps 12 is moved forward to open the grasping portion 17, the tissue portions 50*a* and 50*b* are released from the grasping portion 17. The insertion section 3 of the endoscope 1 may then be retreated. If so, the receiving sheet 47 slips out of the groove portion 45 of the cap 19. The receiving sheet 47 is therefore separated from the cap 19.

Figure 10:
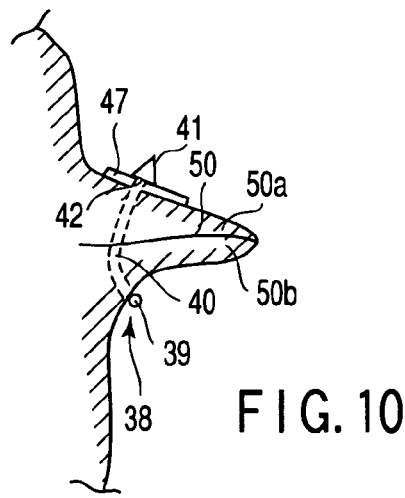
FIG. 10 is a sectional view showing a tissue sutured according to the same embodiment.

Thus, as shown in FIG. 10, the prongs 40 of the staple 38 penetrate the tissue portions 50*a* and 50*b*, the base portion 39 touches the tissue portion 50*b*, and the pointed heads 41 of the prongs 40 touch the receiving sheet 47 which in turn touches the other tissue portion 50*a*. Further, the engaging surfaces 42 of the pointed heads 41 are brought into surface contact with the receiving sheet 47. This prevents the pointed heads 41 from slipping off the receiving sheet 47 and from the tissue portions 50*a* and 50*b*.

In the present embodiment, the cap 19 can easily approach a target region, and the staple 38 crossing the opening portion 31 can suture the tissue portions 50*a* and 50*b*, while the grasping forceps 12 is pulling the tissue portions 50*a* and 50*b* in, through the opening portion 31 of the cap 19. Thus, the target region can be reliably sutured.

Figure 11:
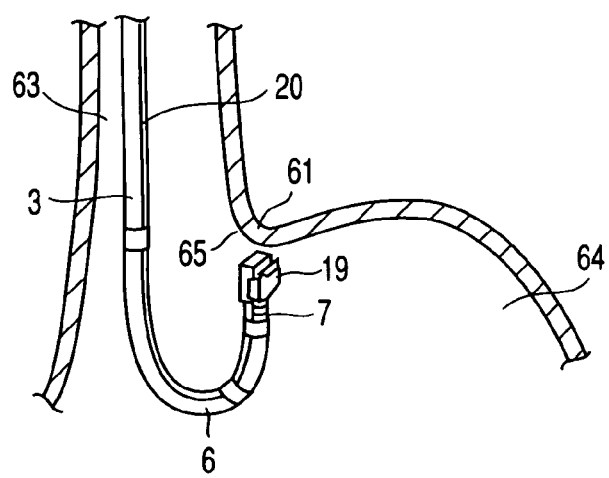
FIG. 11 is a sectional view showing the way the cardiac region is sutured according to a second embodiment of the present invention.
Figure 12:
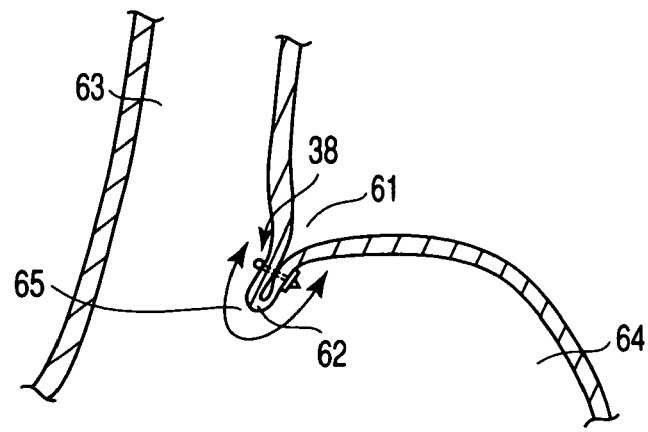
FIG. 12 is a sectional view showing the cardiac region sutured according to the second embodiment.
Figure 13:
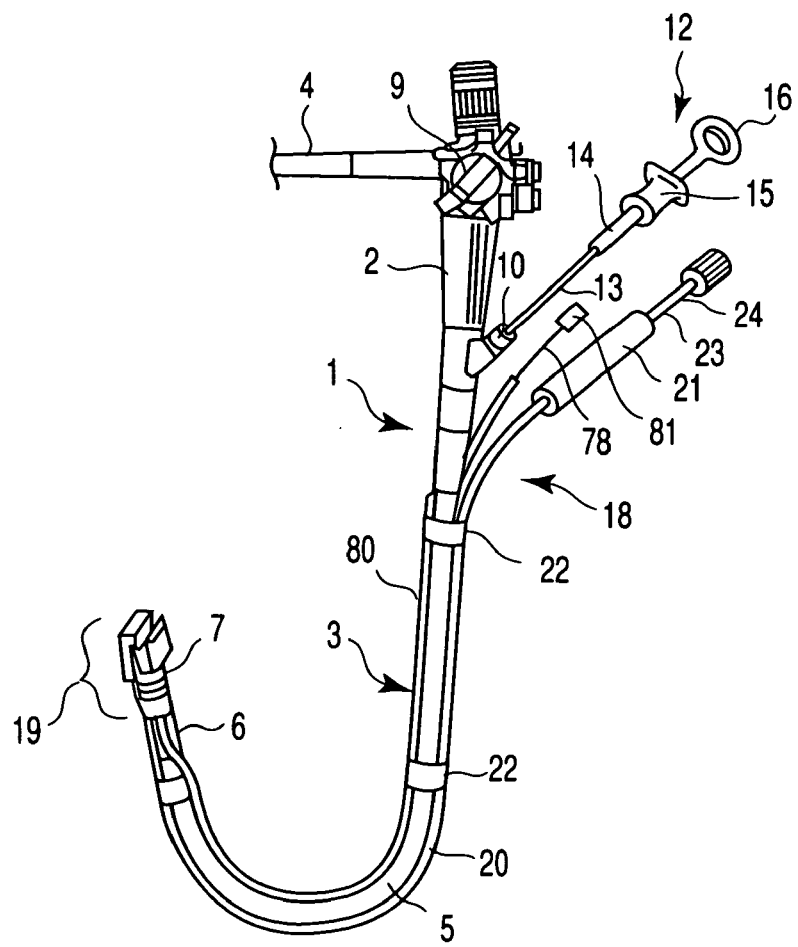
FIG. 13 is a perspective view of an endoscopic suture apparatus according to a third embodiment of the present invention.
Figure 16A:
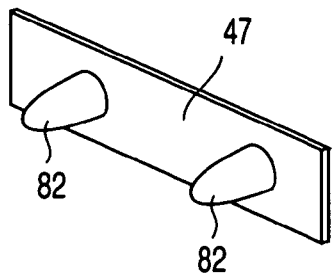
FIG. 16A is a perspective view of a receiving sheet according to the same embodiment.
Figure 16B:
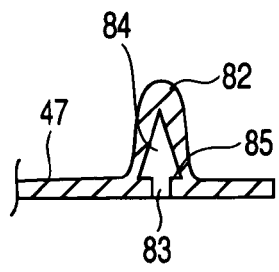
FIGS. 16B and 16C are sectional views of a cover portion.
Figure 16C:
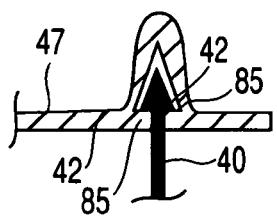
Figure 17:
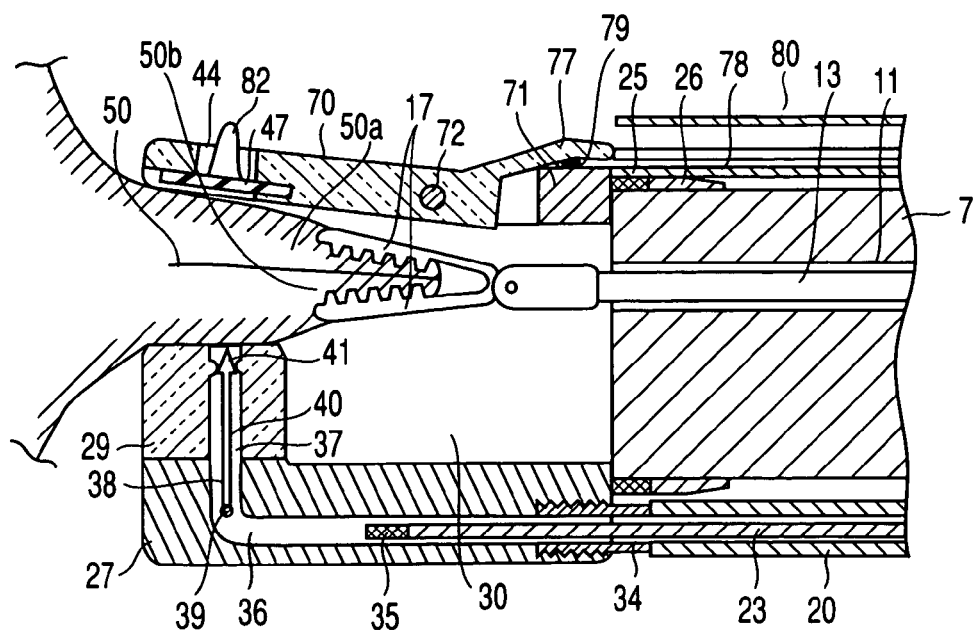
FIG. 17 is a longitudinal sectional side view of the distal end portion of the suture apparatus, showing the function of the same embodiment.

FIGS. 11 and 12 show a second embodiment. In this embodiment, the endoscopic suture apparatus used in the first embodiment is employed to treat patients with a gastro-esophageal reflux disease (GERD). How a bulge portion 62 is formed in a cardiac region 61 will be described. As FIG. 11 shows, the insertion section 3 of the endoscope 1 is inserted into a gullet 63 of the patient, through the mouth and throat. When the insertion section 3 reaches the stomach 64, the bent tube portion 6 is bent substantially, assuming a U shaped, in the stomach 64. The tip portion 7 therefore opposes the cardiac region 61. The cardiac region 61 is observed from below through the endoscope 1.

Then, the control section body 14 of the grasping forceps 12 is operated, projecting the grasping portion 17 ahead of the cap 19, as in the first embodiment. A great-curvature tissue 65 of the cardiac region 61 is held by means of the grasping portion 17. The bulge portion 62 can be formed in the great-curvature tissue 65 as shown in FIG. 12. That is, the great-curvature tissue 65 drawn into the space 30 of the cap 19 by using grasping portion 17, and the staple 38 is stabbed into the great-curvature tissue 65 and secured thereto.

FIGS. 13 to 18 show a third embodiment. The components similar to those of the first and third embodiments are designated at the same reference numerals and will not be described. As FIGS. 14 and 15 depict, a movable base 70, which corresponds to the upper base 28 of the cap 19 used in the first embodiment, is supported on a support base 71 and held by a pivot pin 72 for vertical rocking motion.

More specifically, the support base 71 is formed having a U-shaped plane configuration, and a fitting recess 74 is formed between a pair of support arms 73. The proximal end portion of the movable base 70 has a fitting protrusion 75 that can be fitted in the fitting recess 74. The fitting protrusion 75 is penetrated by the pivot pin 72. The opposite end portions of the pivot pin 72 are rockably inserted in a pin holes 76 that are formed in the support arms 73, individually.

An arm portion 77 is formed integral with the proximal end portion of the fitting protrusion 75 of the movable base 70. The arm portion 77 projects diagonally upward. The arm portion 77 is coupled to the distal end of a control wire 78. An urging spring 79, such as a leaf spring or torsion spring, is provided between the arm portion 77 and the support base 71, and urges the movable base 70 downward so that it extends parallel to the lower base 27.

The control wire 78 can move to pass through a sheath 80 that is coupled to the connecting member 25. The wire 78 is guided to the control section 2 along the insertion section 3 of the endoscope 1. The sheath 80 is made of a flexible material. It can therefore bend as the insertion section 3 is bent. The sheath 80 may be a plastic tube made of, for example, fluoroplastic, polyethylene, polyamide, polyimide, polyurethane, any of various thermoplastic elastomers, or a metallic coil. Alternatively, it may be a plastic tube that is reinforced with a metallic mesh lest it easily kink. Like sheaths 20, the sheath 80 extends along the insertion section 3. It is fixed by medical tape.

A traction control portion 81 is provided on the near-side end of the control wire 78. When the control wire 78 is pulled by the traction control portion 81, the arm portion 77 is pressed down against the urging force of the urging spring 79. When the arm portion 77 is pressed down, the distal end of the movable base 70 rocks upward around the pivot pin 72. The opening portion 31 therefore opens upwards.

The side aperture 44 in the movable base 70 is closed with the receiving sheet 47. The receiving sheet 47 is formed integral with cover portions 82. The portions 82 are shaped like a bullet and provided for the pointed heads 41 of the staple 38, respectively. The receiving sheet 47 has orifices 83 in those parts that face the cover portions 82. The orifices 83 communicate with cover bores 84, individually. The pointed heads 41 of the staple 38 can be inserted into the cover bores 84 through the orifices 83. The engaging surfaces 42 can engage opening edges 85 of the orifices 83, respectively.

How the third embodiment operate will be described. The components identical to those of the first embodiment will not be described. As the control wire 78 is pulled by means of the traction control portion 81, the grasping portion 17 projects ahead of the cap 19 and holds the tissue portions 50*a* and 50*b*.

When the control wire 78 is pulled, the arm portion 77 is pressed down against the urging force of the urging spring 79. As a result, the distal end side of the movable base 70 rocks upward around the pivot pin 72. The opening portion 31 therefore opens wide upwards.

As the tissue portions 50*a* and 50*b*, both held by the grasping portion 17, are drawn into the space 30 of the cap 19 through the opening portion 31, wide areas of the tissue portions 50*a* and 50*b* can be pulled into the space 30 of the cap 19.

If the control slider 24 moves forward, with the puncture control portion 21 of the puncture device 18 supported, the pusher member 23 causes the pusher 35 to advance the staple 38. The pointed heads 41 of the staple 38 get over the ridge portion 43 of the vertical guide bore 37. Then, they project into the opening portion 31 through the vertical guide bore 37.

Thus, the staple 38 is stabbed into the tissue portions 50a and 50b drawn into the space 30 of the cap 19. The pointed heads 41 penetrate the tissue portions 50a and 50b. The pointed heads 41 also penetrate the orifices 83 of the receiving sheet 47 to be inserted into the cover bores 84. Then, the engaging surfaces 42 of the pointed heads 41 engage the opening edges 85 of the orifices 83. Thus, they are prevented from slipping out.

In the present embodiment, the wide areas of the tissue portions 50a and 50b can be pulled into the cap 19, while the movable base 70 is opening the opening portion 31 of the cap 19 wide. Further, the cover portions 82 of the receiving sheet 47, which envelops the pointed heads 41 of the staple 38, can protect other tissues without allowing the pointed heads 41 of the staple 38 to be exposed in the body cavity. The movable base 70 that corresponds to the upper base 28 is rotated in this embodiment. Nevertheless, the lower base 27 may be rotated instead.

Figure 18A:
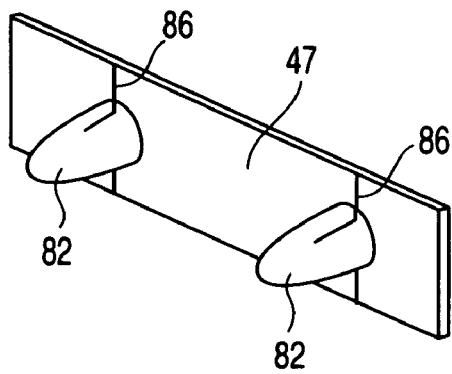
FIG. 18A is a perspective view of a receiving sheet according to a modification of the same embodiment.
Figure 18B:
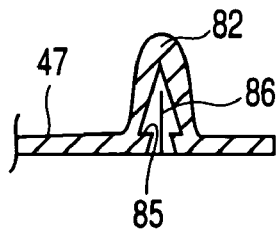
FIG. 18B is a sectional view of a cover portion.
Figure 19:
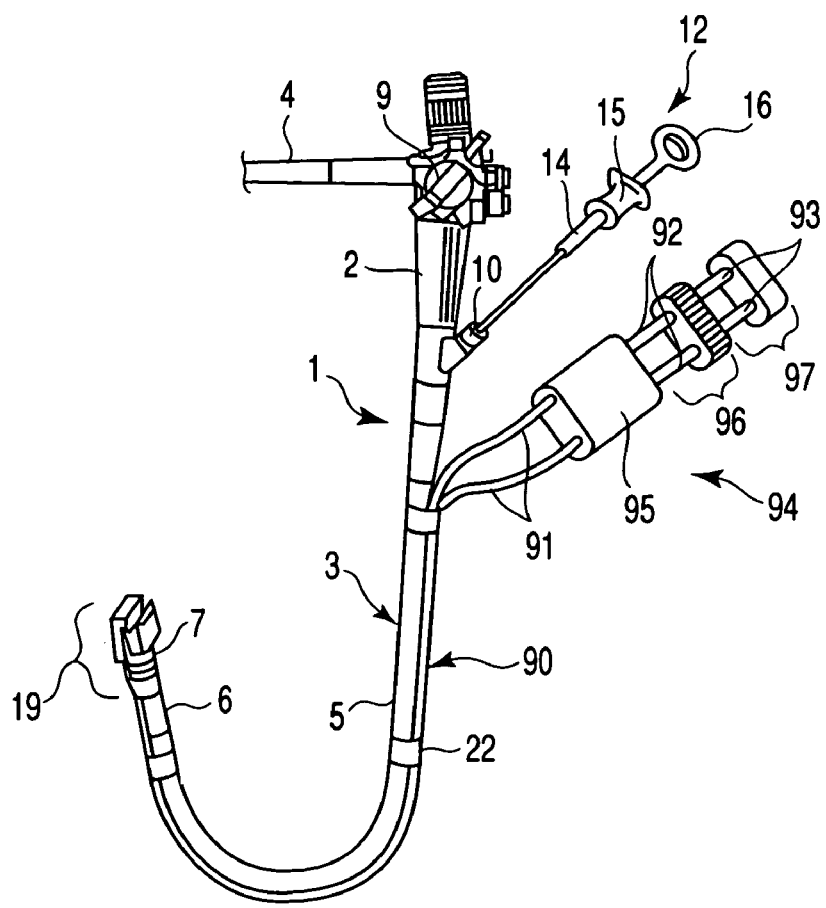
FIG. 19 is a perspective view of an endoscopic suture apparatus according to a fourth embodiment of the present invention.

FIG. 18 shows a modification of the receiving sheet 47. Slits 86 are provided extending from regions around the orifices 83 of the receiving sheet 47, to the respective sidewalls of the cover portions 82. Thus arranged, the slits 86 spread as the pointed heads 41 of the staple 38 penetrate the orifices 83 of the receiving sheet 47. The pointed heads 41 can therefore penetrate the receiving sheet 47 for a reduced resistance.

FIGS. 19 to 25 show a fourth embodiment. The components similar to those of the first and fourth embodiments are designated at the same reference numerals and will not bed described.

The insertion section 3 of the endoscope 1 has a puncture device 90. The puncture device 90 comprises two sheaths 91, hollow needles 92, pusher members 93, and a puncture control portion 94. The sheaths 91 are arranged along the insertion section 3 of the endoscope 1. The hollow needles 92 can move, passing through the sheaths 91. The pusher members 93 are formed of metallic wires or the like and can move, passing through the hollow needles 92. The puncture control portion 94 is provided on the respective near-side ends of the sheaths 91.

The sheaths 91 are formed of flexible material and can bend as the insertion section 3 is bent. It may be a plastic tube made of, for example, fluoroplastic, polyethylene, polyamide, polyimide, polyurethane, any of various thermoplastic elastomers, or a metallic coil. Alternatively, the sheaths 91 may be plastic tubes that are reinforced with a metallic mesh lest it should easily kink. The hollow needles 92 are made of metal having elastic restoring force, such as Nitinol, stainless steel, etc.

The puncture control portion 94 comprises a control portion body 95, a needle slider 96, and a pusher slider 97. The control portion body 95 is provided on the respective near-side ends of the two sheaths 91 and connects the sheaths 91. The needle slider 96 is provided on the respective near-side ends of the two hollow needles 92 and connects and moves the hollow needles 92. The-pusher slider 97 is provided on the respective near-side ends of the two pusher members 93 and connects and moves the pusher members 93.

The lower base 27 of the cap 19 has two guide bores 98 for the two hollow needles 92. A bent guide bore 99 connects the guide bores 98 to a vertical guide bore 100 that is provided in the tip base 29. The hollow needles 92 can move forward and back in the guide bores 98, bent guide bore 99, and vertical guide bore 100. Slits 101 are cut in the inner surface of the vertical guide bore 100, each extending in the vertical direction inside. Namely, the slits 101 are provided on the side of the space 30 of the cap 19.

As FIG. 23B shows, the hollow needles 92 are so sharp that their respective distal end portions can be easily stabbed into the tissue portions 50a and 50b. The needles 92 have slits 102 that extend axially from the distal end portions. A staple 103 is held in the respective distal end portions of the hollow needles 92.

The staple 103 is made of material having flexibility and good bio-compatibility. It may be made of synthetic resin such as nylon 6, nylon 66 or the like. The staple 103 comprises a pair of rod-shaped stopper members 104 and a U-shaped bridge portion 105 that connects these stopper members 104.

The staple 103 is formed by the following method. First, an H-shaped member 117 shown in FIG. 23C, which has the stopper members 104 provided integrally on the opposite ends of a central portion 116, is formed by injection molding. Then, the bridge portion 105 is formed by stretching the central portion 116. The stretched portion is bent into an U-shaped member by means of thermoforming. Preferably, the degree of stretching of the central portion 116 should range from 120 to 500%. This method can provide the stopper members 104 and the bridge portion 105 formed integral with each other. The manufacturing cost is therefore low. Having been stretched, the bridge portion 105 exhibits high tensile strength. The stopper members 104 of the staple 103 are inserted into the hollow needles 92 through their respective distal end portions. The bridge portion 105 projects outside through the slits 102.

How the fourth embodiment operates will be described.

Figure 24:
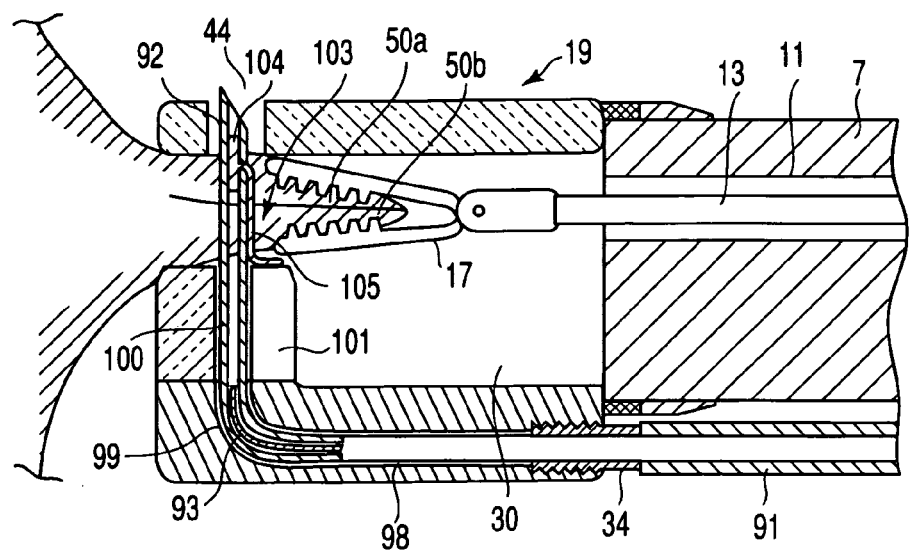
FIG. 24 is a longitudinal sectional side view of the distal end portion of the suture apparatus, showing the function of the same embodiment.

As in the first embodiment, the grasping portion 17 holds the tissue portions 50a and 50b. The tissue portions 50a and 50B are drawn into the space 30 of the cap 19. After the tissue portions 50a and 50b are drawn into the space 30, the needle slider 96 of the puncture control portion 94 is moved forward. The two hollow needles 92 therefore advance. The guide bores 98, bent guide bore 99, and vertical guide bore 100 guide the hollow needles 92 that are advancing. As FIG. 24 depicts, the hollow needles 92 holding the staple 103 penetrate the tissue portions 50a and 50b and project from the side aperture 44.

As the pusher slider 97 advances in this way, the pusher members 93 moves forward in the hollow needles 92. The distal ends of the pusher members 93 push the stopper members 104 of the staple 103 forward. When the stopper members 104 project from the respective distal end portions of the hollow needles 92, the stopper members 104 extend perpendicular to the bridge portion 105 by virtue of elastic restoring force. They are located in the side aperture 44.

Figure 25:
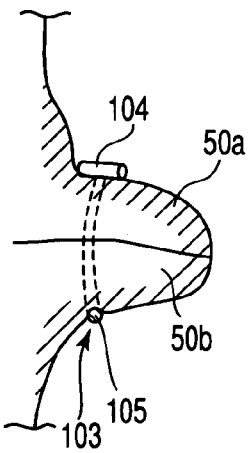
FIG. 25 is a sectional view showing a tissue sutured according to the same embodiment.

If the needle slider 96 is then retreated, drawing the hollow needles 92 out of the tissue portions 50a and 50b. Only the staple 103 remains in the tissue portions 50a and 50b. The stopper members 104 touch the flank of the one tissue portion 50a, while the bridge portion 105 touches the flank of the other tissue portion 50b, as shown in FIG. 25. Thus, the staple is prevented from slipping off. The suture is thus completed.

The staple 103 has the stopper members 104 that are formed integral with it. Hence, it is not necessary to arrange a receiving sheet 47 at the upper base 28 as in the first embodiment. The suture can be performed in the present embodiment, without the upper base 28.

Figure 26:
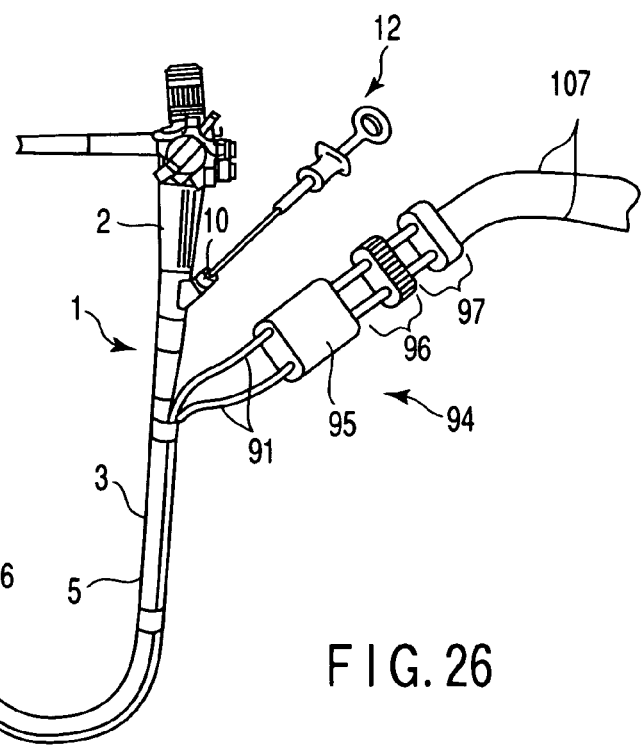
FIG. 26 is a perspective view of an endoscopic suture apparatus according to a fifth embodiment of the present invention.
Figure 27:
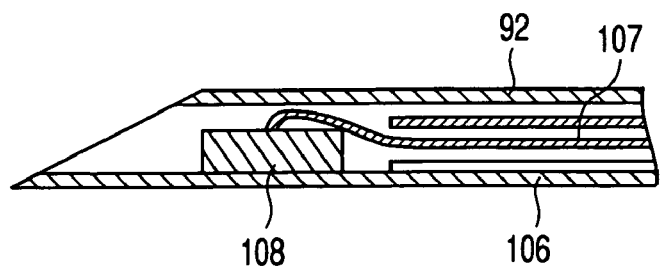
FIG. 27 is a longitudinal sectional side view of the distal end portion of a hollow needle according to the same embodiment.
Figure 28:
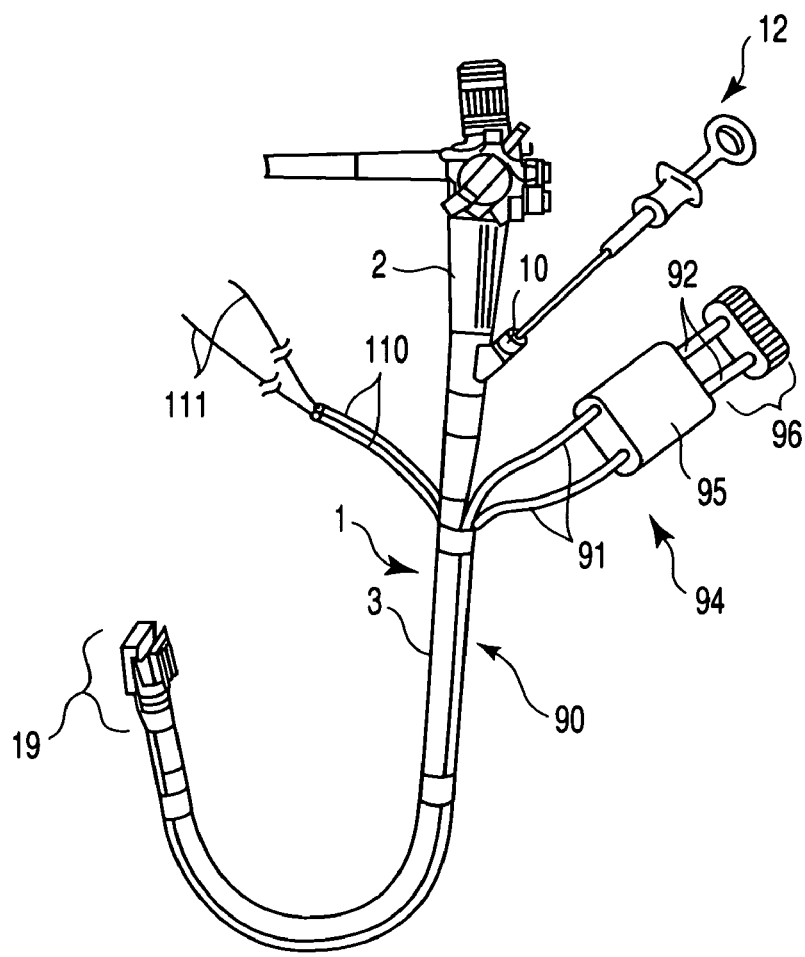
FIG. 28 is a perspective view of an endoscopic suture apparatus according to a sixth embodiment of the present invention.
Figure 29:
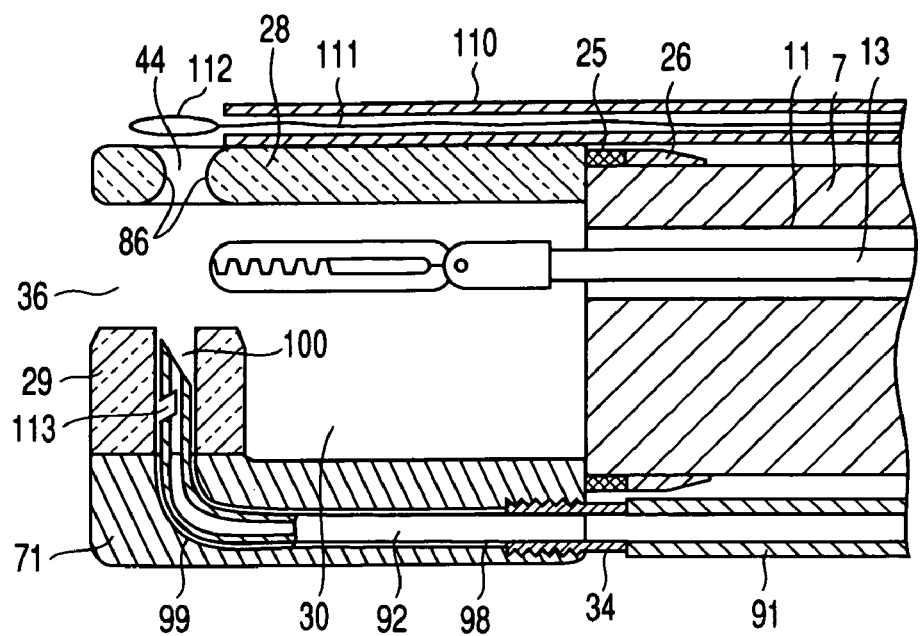
FIG. 29 is a longitudinal sectional side view of the distal end portion of the suture apparatus according to the same embodiment.
Figure 30:
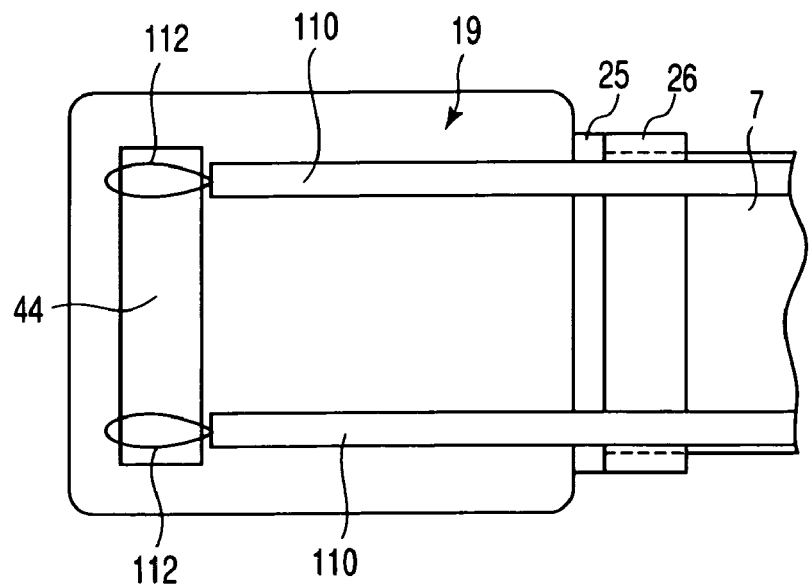
FIG. 30 is a plan view of the distal end portion of the suture apparatus according to the same embodiment.

FIGS. 26 and 27 show a fifth embodiment. The components similar to those of the first, fourth and fifth embodiments are designated at the same reference numerals and will not be described.

Pipe-shaped pusher members 106 are moved, passing through the two hollow needles 92. The near-side ends of the pusher members 106 are connected to the pusher slider 97. Suture threads 107 are passed through the two pusher members 106, respectively. The respective near-side ends of the suture threads 107 are led out from the pusher slider 97. The respective far-side ends of the suture threads 107 are connected to the respective longitudinal-direction middle portions of rod-shaped stopper members 108 in the respective distal end portions of the hollow needles 92.

How the fifth embodiment operates will be described.

As in the fourth embodiment, the two hollow needles 92 are stabbed into the tissue portions 50a and 50b after the tissue portions 50a and 50b are held by the grasping portion 17 and drawn into the space 30 of the cap 19.

When the hollow needles 92 are drawn out of the tissue portions 50a and 50b by retreating the needle slider 96, the stopper members 108 are left with the suture threads 107 in the tissue portions 50a and 50b in this embodiment. The stopper members 108 contact the flank of the one tissue portion 50a.

The insertion section 3 of the endoscope 1 is then drawn out of the patient's body cavity. The respective near-side ends of the two suture threads 107 are thereby exposed outside the patient's body. The suture threads 107 are then tied to form a knot (not shown) outside the patient's body. The knot may be any one that is generally used in a surgical operation.

The knot is passed through the forceps channel 11 of the endoscope 1. This done, the endoscope 1 is inserted into the patient's body cavity and pushed into the patient's body cavity, by using a conventional knot pusher. When the knot reaches a region near the tissue portion 50b, the knot pusher is pressed on to the tissue portion 50b. At the same time, the opposite ends of the suture threads 107 are pulled, fixing the knot.

The operation described above is performed once or a plurality of times. The knot is thereby firmly fixed lest it should be untied. Finally, those parts of the suture threads 107 which are situated on the hand side of the knot are cut by using an endoscopic scissors-type forceps or the like. The remaining parts of the suture threads 107 are recovered from the patient's body. Thereafter, the endoscope 1 and the knot pusher are drawn from the patient's body. The suture is thus completed.

In the present embodiment, the knot can be formed, with the length of the suture threads 107 adjusted to the size of the tissue portions 50a and 50b, especially their thickness. Thus, the tissue portions 50a and 50b can be sutured securely.

FIGS. 28 to 34A, 34B and 34C show a sixth embodiment. The component similar to those of the first, fourth and sixth embodiments are designated at the same reference numerals and will not be described.

The insertion section 3 of the endoscope 1 has the puncture device 90. The puncture device 90 comprises two sheaths 91, hollow needles 92, and puncture control portion 94. The sheaths 91 extend along the insertion section 3 of the endoscope 1. The hollow needles 92 can move, to pass through the sheaths 91. The puncture control portion 94 is provided on the respective near-side ends of the hollow needles 92.

The puncture control portion 94 comprises control portion a body 95 and a needle slider 96. The control portion body 95 is provided on the respective near-side ends of the two sheaths 91 and connects the sheaths 91. The needle slider 96 is mounted on the respective near-side ends of the two hollow needles 92. The slider 96 connects and moves the hollow needles 92. In addition to the sheaths 91, two suture thread sheaths 110 are attached to the insertion section 3 of the endoscope 1. The distal ends of the suture thread sheaths 110 are coupled to the upper base 28. Suture threads 111 are passed through the suture thread sheaths 110, respectively. The far-side ends of the suture threads 111 extend to the side aperture 44 of the cap 19. Loop portions 112 are formed on the respective far-side end portions of the suture threads 111, respectively. The loop portions 112 therefore face the side aperture 44. Notch portions 113 on which the loop portions 112 are to be hooked individually are cut near the far-side ends of the two hollow needles 92. The opposite ends of the side aperture 44 have curved surfaces 86.

How the sixth embodiment operates will be described.

In the sixth embodiment, the suture threads 111 are passed through the suture thread sheaths 110 in advance. The insertion section 3 of the endoscope 1 is inserted into the patient's body cavity, with the loop portions 112 mounted on the far-side ends of the threads positioned in the side aperture 44 of the cap 19.

Figure 31:
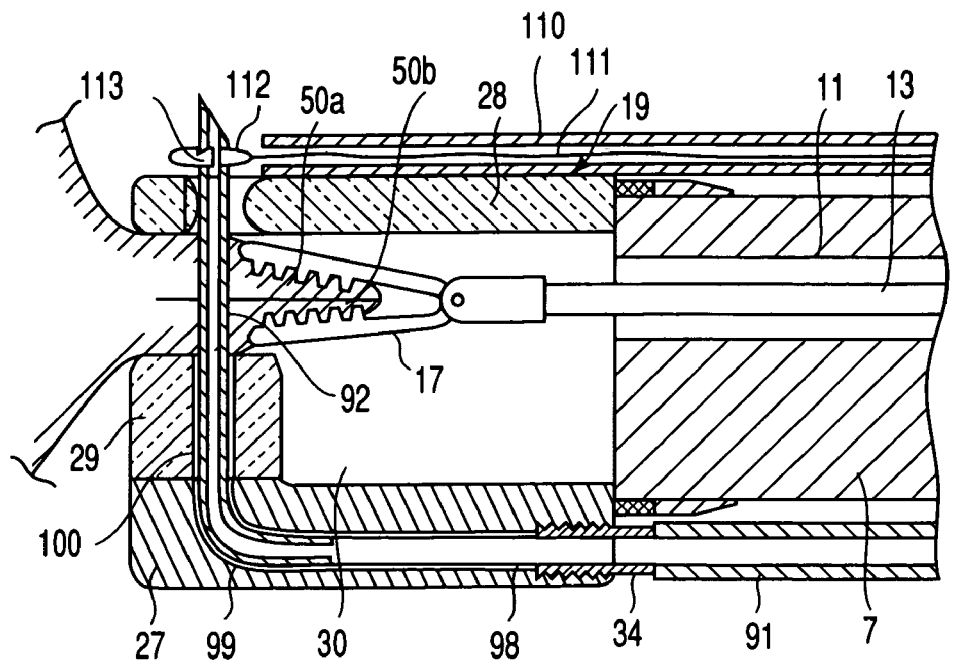
FIG. 31 is a longitudinal sectional side view of the distal end portion of the suture apparatus, showing the function of the same embodiment.

As in the first and fourth embodiments, the tissue portions 50a and 50b are held by the grasping portion 17 and drawn into the space 30 of the cap 19. The needle slider 96 of the puncture control portion 94 is moved forward after the tissue portions 50a and 50b are drawn into the space 30 of the cap 19. The two hollow needles 92 advance simultaneously. The hollow needles 92 are guided through the guide bores 98, bent guide bore 99, and vertical guide bore 100 as they advance. As FIG. 31 shows, the hollow needles 92 that hold the staple 103 penetrate the tissue portions 50a and 50b and project from the side aperture 44.

Figure 32:
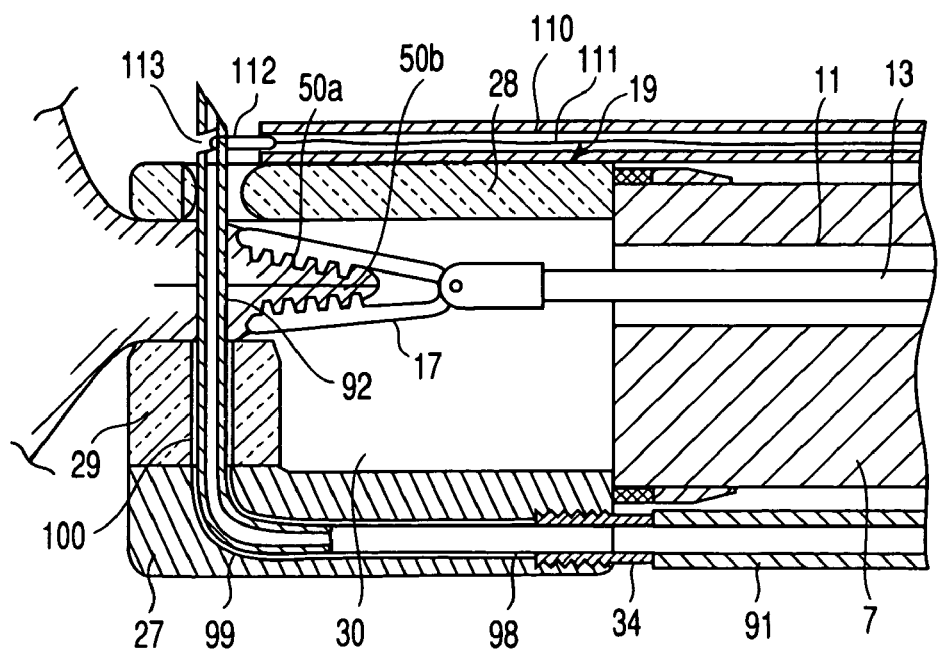
FIG. 32 is a longitudinal sectional side view of the distal end portion of the suture apparatus, showing the function of the same embodiment.

The loop portions 112 are opposed to the side aperture 44 as this is done. The respective far-side ends of the hollow needles 92 therefore pass through the loop portions 112, respectively. The notch portions 113 face the loop portions 112. When the suture threads 111 are drawn in on the side of the control section 2 of the endoscope 1 in this state, the loop portions 112 are anchored to the notch portions 113, as shown in FIG. 32.

The needle slider 96 is then retreated, drawing the hollow needles 92 out of the tissue portions 50a and 50b. Only the two suture threads 111 are left in the tissue portions 50a and 50b, as shown in FIG. 33.

The insertion section 3 of the endoscope 1 is then drawn out of the body cavity. The two suture threads 111 pass through the tissue portions 50a and 50b. Finally, the opposite end portions of the two suture threads 111 are exposed outside the patient's body, as shown in FIG. 34A. The two suture threads 111 so far remaining in the suture thread sheaths 110 are first tied to form a first knot 114 outside the patient's body.

If the suture threads 111 having so far been in the hollow needles 92 are then drawn out to the hand side, the first knot 114 is introduced into the body cavity and touch the flank of the one tissue portion 50a, as shown in FIG. 34B.

In this state, the suture threads 111 having so far been in the hollow needles 92 are tied to form a second knot 115 outside the patient's body. This second knot 115 is passed through the forceps channel 11 of the endoscope 1, and the endoscope 1 is inserted into the patient's body cavity and pushed into the patient's body cavity by means of the conventional knot pusher. When the second knot 115 reaches a region near the tissue portion 50b, the knot pusher is pressed against the tissue portion 50b. At the same time, the opposite ends of the suture threads 111 are pulled, and the second knot 115 is fixed.

The above-described operation is carried out once or repeated a plurality of times, and the second knot 115 is firmly fixed lest it be untied. If those parts of the suture threads 111 which are situated on the hand side of the second knot 115 are finally cut by means of the endoscopic scissors-type forceps or the like, the tissue portions 50*a* and 50*b* are sutured, as shown in FIG. 34C. Finally, the remaining parts of the suture threads 111 are recovered from the patient's body, and the endoscope 1 and the knot pusher are drawn out of the patient's body, whereupon the suture is completed.

While the suture threads 111 must be substantially twice as long as the insertion section 3 of the endoscope 1, according to the present embodiment, the tissue portions 50*a* and 50*b* can be securely sutured with the suture threads 111 without regard to the size of the tissue portions 50*a* and 50*b*, especially their thickness.

As an application of the endoscopic suture apparatus described above, mucous membranes around a region that are subjected to endoscopic mucosal resection are gathered to cover the incised region and sutured, in some cases.

The following is a description of an example of endoscopic mucosal resection. First, the configuration of an injection needle 201 for injecting a local parenteral solution under a mucous membrane and forming an orifice in the mucous membrane will be described with reference to FIGS. 35 to 37.

Figure 35:
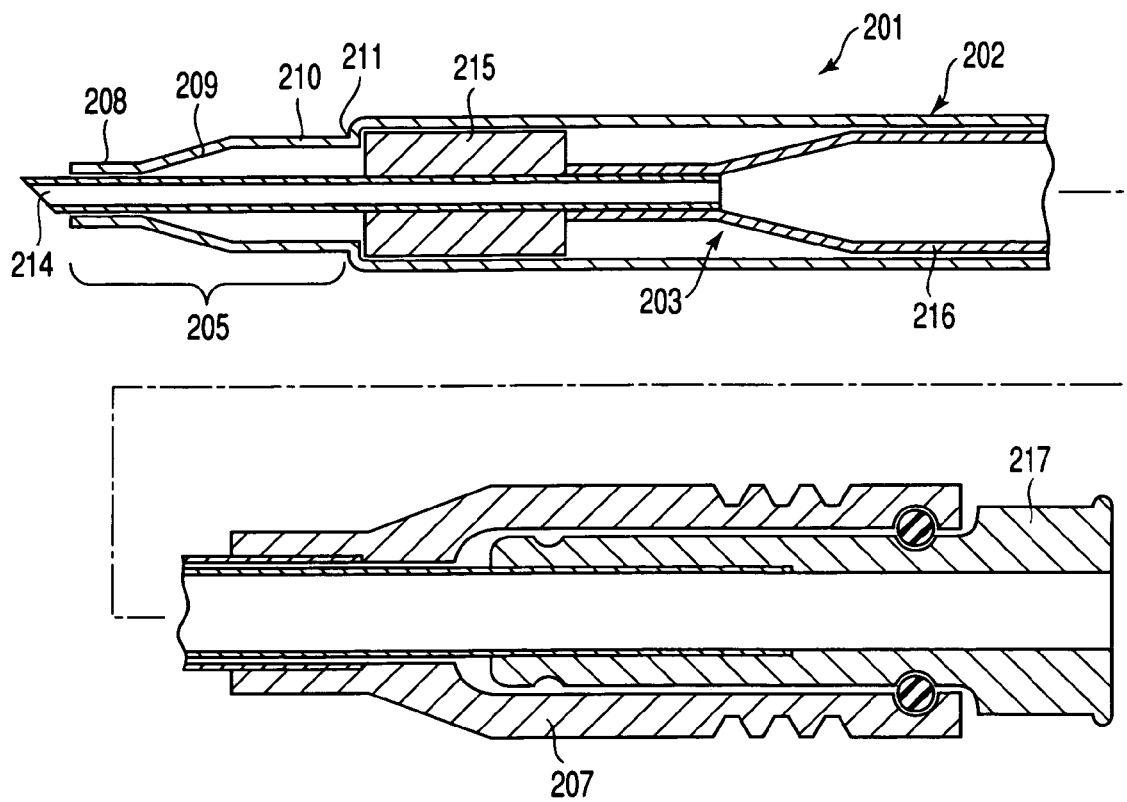
FIG. 35 is a longitudinal sectional side view of an injection needle for endoscopic mucosal resection.
Figure 36:
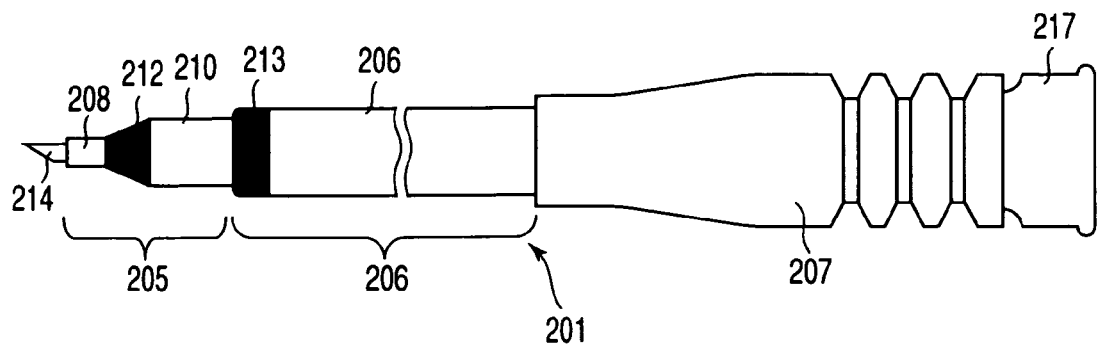
FIG. 36 is a side view of the injection needle.

As shown in FIGS. 35 and 36, the injection needle 201 comprises an elongate outer sheath 202 formed of a flexible tube and an inner sheath 203 also formed of a flexible tube.

The outer sheath 202 is composed of a distal end portion 205, an insertional portion 206, and a hand-side portion 207. Preferably, the outer sheath 202 should be formed of a highly flexible material such as PTFE. Preferably, moreover, the outside and inside diameters of the insertional portion 206 should range from φ1.5 mm to φ4.0 mm and from φ1.0 mm to φ3.5 mm, respectively.

Figure 37:
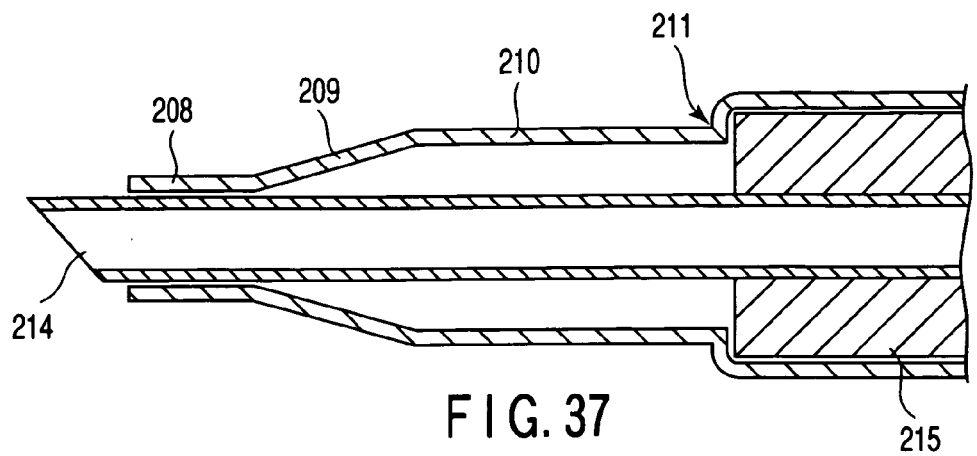
FIG. 37 is a longitudinal sectional side view of the distal end portion of the injection needle.

As shown in FIG. 37, the distal end portion 205 is composed of an initial-insertion portion 208, taper portion 209, dilation portion 210, and stopper 211. The distal end portion 205 may be integral with or separate from the insertional portion 206. Preferably, the distal end portion 205 should be formed of a highly flexible material. Preferably, the outside and inside diameters of the initial-insertion portion 208 should range from φ0.7 mm to φ2.0 mm and from φ0.5 mm to φ1.8 mm, respectively. Preferably, moreover, the length of the initial-insertion portion 208 should range from 0.5 mm t 5 mm. The outside and inside diameters of the dilation portion 210 should range from φ1.5 mm to 4 mm and from 1.3 mm to 3.8 mm, respectively. Further, the outside diameter of the dilation portion 210 is larger than the outside diameter of the initial-insertion portion 208. Furthermore, the outside diameter of the dilation portion 210 is smaller than the outside diameter of the insertional portion 206. Preferably, moreover, the length of the dilation portion 210 should range from 1 mm to 10 mm.

A stopper 211 is provided so as to connect the proximal end of the dilation portion 210 and the distal end of the insertional portion 206. The stopper 211 extends substantially at right angles to the axial direction of the dilation portion 210 and the insertional portion 206. The taper portion 209 smoothly connects the initial-insertion portion 208 and the dilation portion 210. Preferably, moreover, the length of the taper portion 209 should range from 1 mm to 10 mm.

The taper portion 209 and the distal end portion of the insertional portion 206 are figured with a first marking 212 and a second marking 213, respectively. Further, the first marking 212 and the second marking 213 may be of any different colors or the same color. The respective shapes of the markings are not limited to the ones shown in FIG. 36. If the boundary between the initial-insertion portion 208 and the taper portion 209 can be recognized with ease, moreover, the first marking 212 may be formed on the proximal end portion of the initial-insertion portion 208, for example. Alternatively, the initial-insertion portion 208 and the taper portion 209 may be coated in different colors. If the boundary between the dilation portion 210 and the insertional portion 206 can be recognized with ease, furthermore, the marking configurations are not limited to the aforesaid ones. For example, the second marking may be formed on the proximal end portion of the dilation portion 210, or the dilation portion 210 and the insertional portion 206 may be coated in different colors. If the boundaries between individual components can be recognized with ease, the number of markings is not limited to two, naturally.

The following is a description of the inner sheath 203. The inner sheath 203 is composed of a needle 214, needle stopper 215, liquid feed tube 216, and hand-side control portion 217. Preferably, the outside and inside diameters of the liquid feed tube 216 should range from φ0.8 mm to φ3.3 mm and from φ0.6 mm to 3 mm, respectively. The needle 214 is fixed to the liquid feed tube 216 by adhesive bonding on the distal end side of the liquid feed tube 216, and is further fixed to the needle stopper 215 by adhesive bonding on the distal end side of the liquid feed tube 216. The needle 214 and the needle stopper 215 may be fixed by thermal welding or the like instead of being fixed by adhesive bonding.

The liquid feed tube 216 is fixed to the hand-side control portion 217 by adhesive bonding on the hand side. The inner sheath 203 can be slid in the outer sheath 202 by moving the hand-side control portion 217 back and forth. Further, the needle stopper 215 restricts the length of projection of the needle 214 from the outer sheath 202 by interfering with the stopper 211 of the outer sheath 202.

Figure 38:
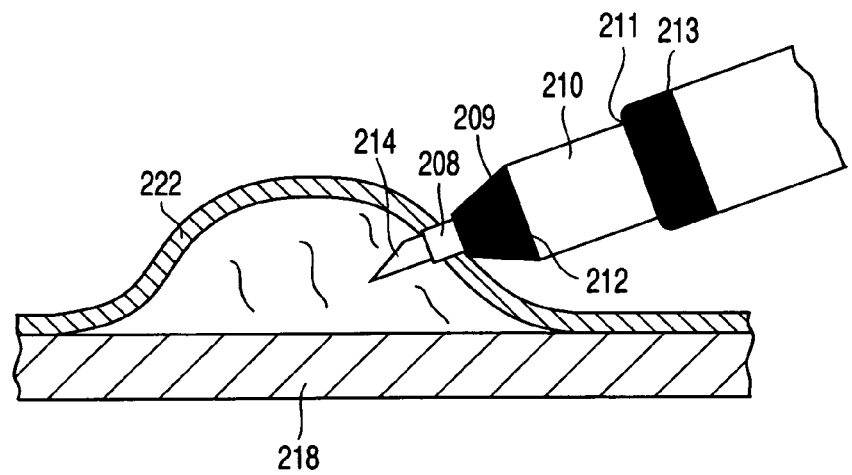
FIG. 38 is a view illustrating operation for endoscopic mucosal resection.

The operation of the injection needle 201 will now be described with reference to FIGS. 38 to 42. First, the endoscope (not shown) is inserted into a target region, and the injection needle 201 is caused to project from the distal end of the endoscope, as shown in FIG. 38. Thereafter, the needle 214 is caused to project from the distal end portion of the outer sheath 202 of the injection needle 201, and a physiological saline or other solution is injected under a mucous membrane 222 of an organ by means of the needle 214. The higher the viscosity of the solution, the longer the bulging time of the mucous membrane 222 is. Thus, a procedure can be carried out with safety. A highly viscous liquid can be fed easily if the inside diameter of the liquid feed tube 216 is large enough. As this is done, the initial-insertion portion 208 of the outer sheath 202 is also inserted under the mucous membrane in advance. Since the first marking 212 clearly defines the boundary between the initial-insertion portion 208 and the taper portion 209, moreover, the initial-insertion portion 208 alone can be easily inserted under the mucous membrane.

Figure 39:
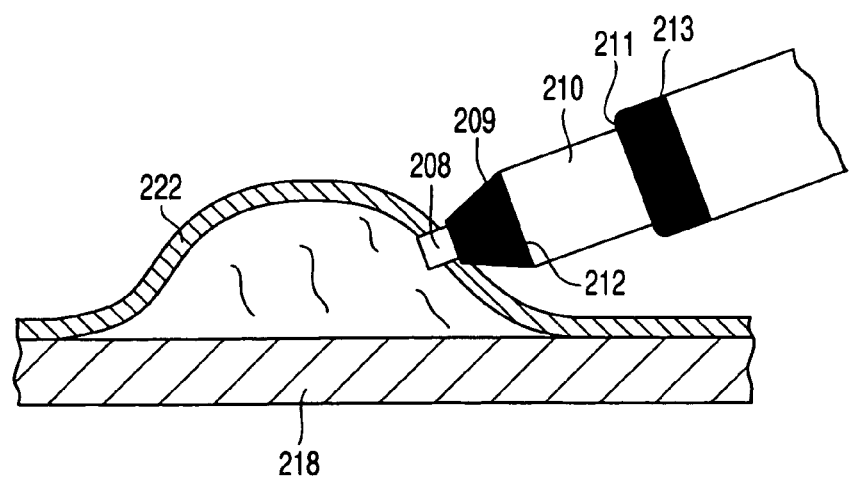
FIG. 39 is a view illustrating the operation for endoscopic mucosal resection.

Then, the needle 214 is pulled into the outer sheath 202 by operating the hand-side control portion 217, as shown in FIG. 39. As this is done, the initial-insertion portion 208 alone underlies the mucous membrane. Since the initial-insertion portion 208 is long enough, it can never slip out from under the mucous membrane at that time.

Then, the outer sheath 202 is pushed in to the depth of the dilation portion 210, as shown in FIG. 40. The taper portion 209 is smooth enough to allow the outer sheath 202 to be easily pushed into it. As this is done, the needle 214 is held in the outer sheath 202, and besides, the distal end portion 205 is soft enough, so that a muscularis 218 cannot be damaged when the structure is pushed in.

Further, the second marking 213 clearly defines the boundary between the dilation portion 210 and the insertional portion 206, and the stopper 211 is caught by the mucous membrane 222, so that the outer sheath 202 cannot be inserted too deep. After the outer sheath 202 is inserted to the depth of the dilation portion 210, the outer sheath 202 is drawn out from under the mucous membrane. As this is done, an orifice 219 is bored in the mucous membrane 222, as shown in FIG. 41. Thereafter, the mucous membrane alone is incised by using a diathermy knife 221 described in Jpn. Pat. Appln. KOKAI Publication No. 8-299355, the knife having an insulated tip 220 on its distal end, as shown in FIG. 42, for example. The orifice 219 that is formed by the injection needle 201 is large enough to allow the insulated tip 220 to be easily inserted under the mucous membrane. Thus, only the one injection needle is needed to inject the solution under the mucous membrane and form the orifice, so that the trouble of replacing operative instruments can be saved.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscopic suture apparatus comprising:

a holding member having a connecting portion provided on a proximal end side thereof for connecting the holding member to a distal end portion of an insertion section of an endoscope, the holding member and the distal end portion of the insertion section defining a treatment space, and the holding member having an opening portion provided on a distal end side thereof, through which a living tissue is retreated into the treatment space while the living tissue is urged by the opening portion;

a retreating member configured to be movable to hold the living tissue outside the treatment space and retreat the living tissue into the treatment space through the opening portion;

a puncture member provided for the holding member, the puncture member being relatively movable with respect to the holding member to puncture the living tissue retreated into the treatment space;

a driving member configured to move the puncture member, the driving member being connected to the puncture member on a distal end side and to a puncture control member on a proximal end side; and a suture member configured to puncture the living tissue according to puncture of the puncture member, the suture member suturing the living tissue and kept in a living body;

wherein the suture member is separated from the puncture member and is previously held in the holding member, and the puncture member is forwardly moved to support the suture member on its forward end side.

2. The endoscopic suture apparatus according to claim 1 wherein the puncture member is relatively moved with respect to the holding member in one direction normal to a direction in which the living tissue is retracted into the treatment space.

3. The endoscopic suture apparatus according to claim 1 wherein the opening portion has a diameter smaller than that of the treatment space.

4. The endoscopic suture apparatus according to claim 1 wherein the opening portion is positioned to offset against the treatment space.

5. An endoscopic suture apparatus comprising:

a holding member having a connecting portion provided on a proximal end side thereof for connecting the holding member to a distal end portion of an insertion section of an endoscope, the holding member and the distal end portion of the insertion section defining a treatment space, and the holding member having an opening portion provided on a distal end side thereof, through which a living tissue is retreated into the treatment space;

a puncture member provided for the holding member, the puncture member being relatively movable with respect to the holding member to puncture the living tissue retreated into the treatment space;

a driving member configured to move the puncture member, the driving member being connected to the puncture member on a distal end side and to a puncture control member on a proximal end side;

a pressing member provided for the holding member near the opening portion and to press the living tissue at least when the puncture member punctures the leaving tissue; and a suture member configured to puncture the living tissue according to puncture of the puncture member, the suture member suturing the living tissue and kept in a living body;

wherein the pressing member includes a base member positioned on the forward side of the puncture member in a moving direction thereof to prevent the living tissue to move together with the puncture member when the puncture member moves forwardly in the moving direction and punctures the living tissue.

6. The endoscopic suture apparatus according to claim 5, wherein the pressing member further includes an urging member for urging the base member in a direction opposite to the moving direction of the puncture member.

7. The endoscopic suture apparatus according to claim 5, wherein the treatment space is provided in a distal end portion of the holding member between the opening portion and the insertion section.

8. The endoscopic suture apparatus according to claim 5 wherein the puncture member is relatively moved with respect to the holding member in one direction normal to a direction in which the living tissue is retracted into the treatment space.

9. The endoscopic suture apparatus according to claim 5 wherein the opening portion has a diameter smaller than that of the treatment space.

10. The endoscopic suture apparatus according to claim 5 wherein the opening portion is positioned to offset against the treatment space.

11. A method for suturing a living tissue comprising:

introducing a holding member connected to a distal end of an endoscope on a proximal end side, into a living body, the holding member supporting a suturing member separated from a puncture member and the suturing member being previously held in the holding member;

moving a retreating member outside a treating space formed in a distal end portion of the holding member, holding a living tissue with the retreating member and retreating the held living tissue into the holding member from an opening portion into the treating space, in a state where the living tissue is urged so that opposite sides of living tissue are approached to each other, the living tissue then being kept in the holding member;

forwardly moving the puncture member in a direction for puncturing the living tissue which has been retreated in the treatment space to one side of the opposing sides from the other side thereof with the suturing member, by the puncture member holding the suturing member on its forward side, so that the living tissue is sutured by the suturing member punctured through the living tissue; and removing the holding member from the living body.

* * * * *